United States Patent
Brings et al.

(10) Patent No.: US 11,202,833 B2
(45) Date of Patent: Dec. 21, 2021

(54) METHYLGLYOXAL-SCAVENGING CYCLIC PEPTIDES AND THEIR USE FOR THE PREVENTION AND TREATMENT OF DISEASES ASSOCIATED WITH ELEVATED METHYLGLYOXAL LEVELS

(71) Applicant: RUPRECHT-KARLS-UNIVERSITÄT HEIDELBERG, Heidelberg (DE)

(72) Inventors: Sebastian Brings, Leimen (DE); Thomas H. Fleming, Heidelberg (DE); Walter Mier, Bensheim (DE); Peter P. Nawroth, Leimen (DE)

(73) Assignee: RUPRECHT-KARLS-UNIVERSITÄT HEIDELBERG, Heidelberg (DE)

(*) Notice: Subject to any disclaimer, the term of this patent is extended or adjusted under 35 U.S.C. 154(b) by 104 days.

(21) Appl. No.: 16/345,094

(22) PCT Filed: Nov. 6, 2017

(86) PCT No.: PCT/EP2017/078298
§ 371 (c)(1),
(2) Date: Apr. 25, 2019

(87) PCT Pub. No.: WO2018/087028
PCT Pub. Date: May 17, 2018

(65) Prior Publication Data
US 2019/0282700 A1 Sep. 19, 2019

(30) Foreign Application Priority Data
Nov. 10, 2016 (EP) .................... 16198096

(51) Int. Cl.
*C07K 7/64* (2006.01)
*A61K 47/54* (2017.01)
*G01N 33/566* (2006.01)
*A61K 51/08* (2006.01)
*C07K 7/56* (2006.01)
*C07K 7/06* (2006.01)
*A61K 38/00* (2006.01)

(52) U.S. Cl.
CPC .......... *A61K 47/542* (2017.08); *A61K 51/088* (2013.01); *C07K 7/06* (2013.01); *C07K 7/56* (2013.01); *C07K 7/64* (2013.01); *G01N 33/566* (2013.01); *A61K 38/00* (2013.01)

(58) Field of Classification Search
None
See application file for complete search history.

(56) References Cited

U.S. PATENT DOCUMENTS
2013/0225506 A1 8/2013 Gombert et al.

OTHER PUBLICATIONS

Davies JS ('The cyclization of peptides and depsipeptides' Journal of Peptide Science v9 2003 pp. 471-501) (Year: 2003).*
Oh et al. ('Enhanced cellular uptake of short polyarginine peptides through fatty acylation and cyclization' Molecular Pharmaceutics v11 Jun. 30, 2014 pp. 2845-2854) (Year: 2014).*
Vijayakumar et al. ('Hydrogen bonds between short polar side chains and peptide backbone:prevalence in proteins and effects on helix-forming propensities' Proteins:Structure, Function, and Genetics v34 1999 pp. 497-507) (Year: 1999).*
Acyl Group Definition (Acyl Group Definition retrieved from http://www.chem.ucla.edu/~harding/IGOC/A/acyl_group.html on Sep. 23, 2020, 1 page) (Year: 2020).*
Traboulsi et al. ('Macrocyclic cell penetrating peptides: a study of structure-penetration properties' Bioconjugate Chemistry v26 Feb. 5, 2015 pp. 405-411) (Year: 2015).*
Dhar, Indu et al. "Arginine Attenuates Methylglyoxal- and High Glucose-Induced Endothelial Dysfunction and Oxidative Stress by an Endothelial Nitric-Oxide Synthase-Independent Mechanism," Journal of Pharmacology and Experimental Therapeutics 342(1):196-204, Jul. 1, 2012.

* cited by examiner

*Primary Examiner* — Ronald T Niebauer
(74) *Attorney, Agent, or Firm* — Saliwanchik, Lloyd & Eisenschenk

(57) ABSTRACT

The present invention relates to cyclic peptide compounds which inhibit or antagonize the binding of methylglyoxal (MG) and/or other reactive carbonyl species (RCS) to an arginine- or lysine-containing protein. Preferred scavenger compounds are said cyclic peptides comprising a specific amino acid motif and a hydrophobic modification, and pharmaceutical compositions thereof. The present invention furthermore relates to the use of the cyclic peptides as scavenger or antagonists of methylglyoxal and/or related reactive carbonyl species (RCS). The present invention furthermore relates to the use of the cyclic peptides for the prevention and/or treatment of a disease caused by or associated with methylglyoxal (MG) and/or reactive carbonyl species (RCS), in particular caused by or associated with elevated MG levels, such as diabetes and its associated complications, cardiovascular diseases and obesity.

9 Claims, 13 Drawing Sheets
Specification includes a Sequence Listing.

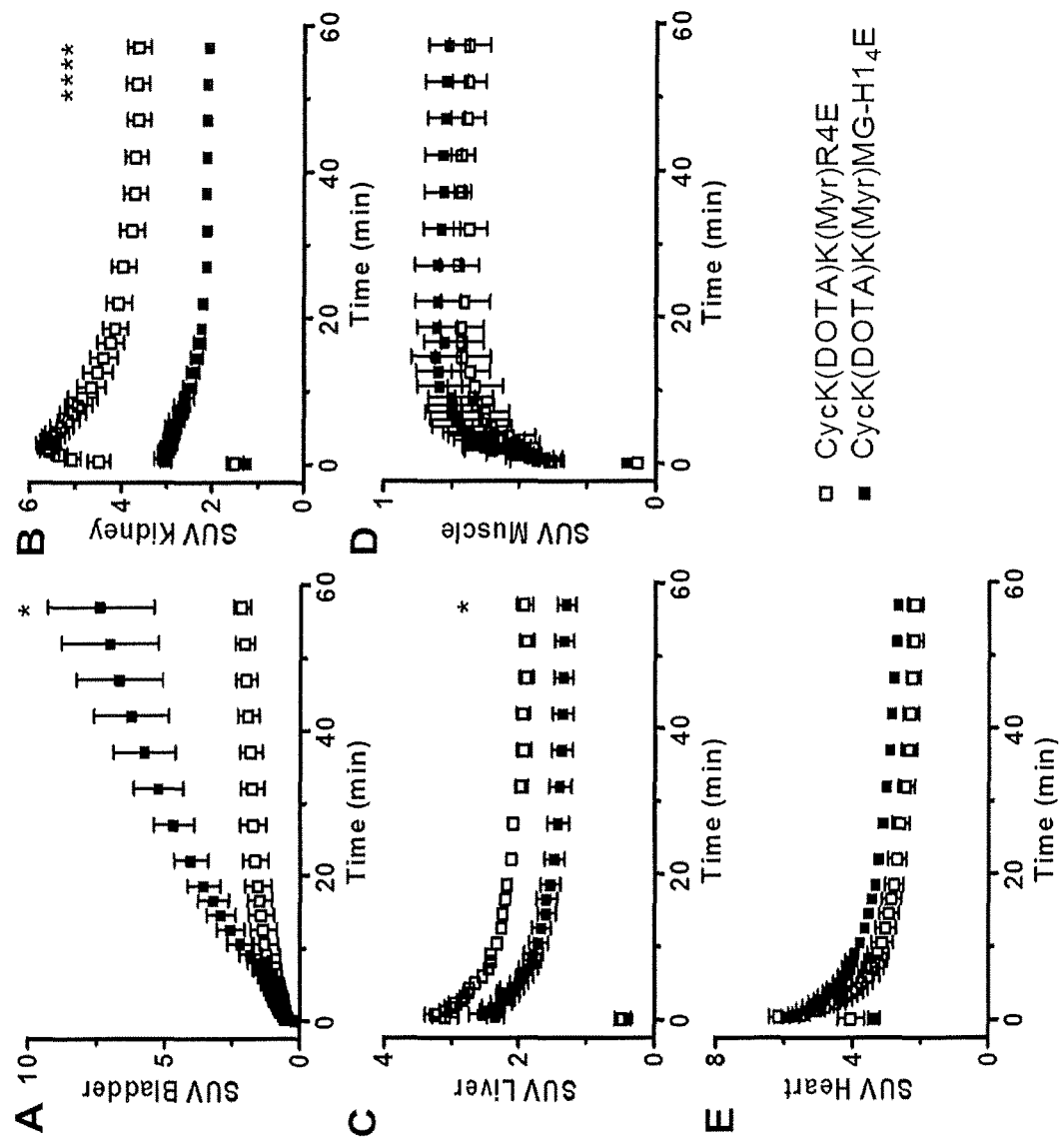
Figure 4 A - E

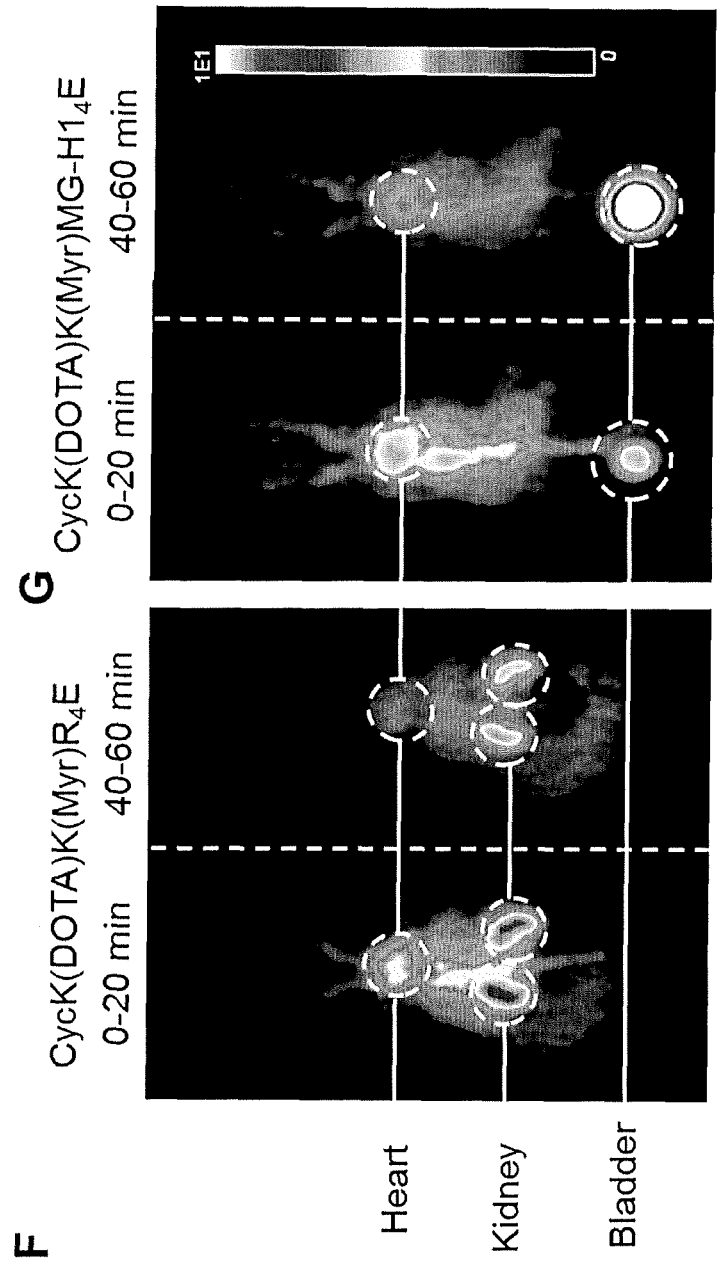
Figure 4 F and G

METHYLGLYOXAL-SCAVENGING CYCLIC PEPTIDES AND THEIR USE FOR THE PREVENTION AND TREATMENT OF DISEASES ASSOCIATED WITH ELEVATED METHYLGLYOXAL LEVELS

CROSS REFERENCE TO RELATED APPLICATIONS

This application is a National Stage Application of International Application Number PCT/EP2017/078298, filed Nov. 6, 2017; which claims priority to European Patent Application No. 16198096.6, filed Nov. 10, 2016.

The Sequence Listing for this application is labeled "SeqList-25Apr19-ST25.txt", which was created on Apr. 25, 2019 and is 5 KB. The entire content is incorporated herein by reference in its entirety.

The present invention relates to cyclic peptide compounds which inhibit or antagonize the binding of methylglyoxal (MG) and/or other reactive carbonyl species (RCS) to an arginine- or lysine-containing protein. Preferred scavenger compounds are said cyclic peptides comprising a specific amino acid motif and a hydrophobic modification, and pharmaceutical compositions thereof. The present invention furthermore relates to the use of the cyclic peptides as scavenger or antagonists of methylglyoxal and/or related reactive carbonyl species (RCS). The present invention furthermore relates to the use of the cyclic peptides for the prevention and/or treatment of a disease caused by or associated with methylglyoxal (MG) and/or reactive carbonyl species (RCS), in particular caused by or associated with elevated MG levels, such as diabetes and its associated complications, cardiovascular diseases and obesity.

BACKGROUND OF THE INVENTION

Diabetes is defined by high blood glucose levels. Despite the high efficacy of the modern standard therapies, diabetic patients develop serious complications in part caused by reactive dicarbonyl compounds. These dicarbonyls form protein adducts termed advanced glycation end-products (AGEs), one of the factors for the development of diabetic complications (Thornalley et al., 2003; Rabbani et al., 2014). Methylglyoxal (MG) represents the most abundant reactive dicarbonyl compound in the plasma of diabetic patients (Fleming et al., 2012). The formation of MG derived protein adducts is associated with diabetic nephropathy, diabetic retinopathy, diabetic neuropathy and endothelial dysfunction (Beisswenger et al. 2005, Beisswenger et al. 2013, Genuth et al. 2015, Maessen et al. 2015, Giacco et al. 2014). Furthermore, MG is involved in the development of cardiovascular complications (Schalkwijk et al. 1998, Rabbani et al. 2010, Rabbani et al. 2011). There it contributes to atherosclerosis via modification of low density lipoprotein, increasing its atherogenicity while affecting binding to- and thus clearance via the LDL receptor. With regard to diabetic neuropathy we have previously shown that MG is causative of hyperalgesia, an increased sensitivity towards pain, associated with diabetic neuropathy (Bierhaus et al., 2012). Additional support for a deleterious effect of MG on neurons during development comes from a study of maternal diabetes in mice (Yang, Cancino et al. 2016). The MG detoxifying enzyme glyoxalase 1 (Glo1) is also decreased in adipose tissue while overexpression of Glo1 suppresses weight gain linking MG to adiposity (Rabbani and Thornalley 2015).

Additional diseases where an pathogenic effect of MG is emerging and where said compound may be of therapeutic potential are Alzheimer's Disease (Hensley et al. 1995, Aksenov et al. 2000, Conrad et al. 2000, Aksenov et al. 2001, Butterfield and Lauderback 2002, Castegna et al. 2002, Choi et al. 2002, Munch et al. 2003, Ahmed et al. 2005, Chen et al. 2007), amyotrophic lateral sclerosis (Shinpo et al. 2000, Ferrante et al. 1997), cataractogenesis (Boscia et al. 2000, Shamsi et al. 1998), chronic renal failure and chronic or acute Uraemia (Miyata et al. 1999, Himmelfarb et al. 2000, Himmelfarb and McMonagle 2001, Lim et al. 2002, Agalou et al. 2003, Lapolla et al. 2005, Rabbani et al. 2007, Muller-Krebs et al. 2008, Nakayama et al. 2008), cystic fibrosis (McGrath et al. 1999, Range et al. 1999), dementia with Lewy bodies (Lyras et al. 1998), ischaemia-reperfusion (Pantke et al. 1999), pre-eclempsia (Zusterzeel et al. 2001), psoriasis (Dimon-Gadal et al. 2000), rheumatoid arthritis and juvenile chronic arthritis (Mantle et al. 1999, Renke et al. 2000), severe sepsis (Winterbourn et al. 2000, Abu-Zidan et al. 2002), systemic amyloidosis (Miyata et al. 2000) and Parkinson's Disease (Floor and Wetzel 1998).

Thus, therapeutic lowering of MG levels is a promising approach to treat diabetic complications in particular diabetic neuropathy as well as other diseases associated with deregulation of Glo1 and/or increased MG levels. Consequently, numerous small molecule scavengers of MG have been developed. However, none of these compounds has been proven successful in clinical trials due to side effects or lack of efficacy (Forbes et al., 2013; Maessen et al., 2015; Engelen et al., 2013).

The scavenging reaction is a comparably slow process, therefore, the ideal scavenger has to have a long circulation time, combined with a reactivity which is specific to avoid aberrant activity (Lo et al., 1994).

The present invention aims to provide means and methods for scavenging and/or antagonizing methylglyoxal and/or reactive carbonyl species (RCS), which allow an improved prevention and/or treatment of pain, in particular pain and/or hyperalgesia caused by or associated with methylglyoxal and/or reactive carbonyl species (RCS) as well as the treatment of other diseases associated with excessive MG formation and/or GLO1 deregulation, such as diabetic nephropathy and diabetic retinopathy, endothelial dysfunction and cardiovascular diseases.

SUMMARY OF THE INVENTION

According to the present invention this object is solved by providing a cyclic peptide comprising the amino acid sequence of

$$Xaa_m\text{-}(Arg)_n\text{-}Glu_o$$

wherein Xaa is selected from Lys, ornithine (2,5-diaminopentanoic acid), 2,4-diaminobutanoic acid, 2,3-diaminopropanoic acid, m is at least 1,
n is selected from 2 to 8,
o is 0 or 1,
and a hydrophobic modification.

According to the present invention this object is solved by providing the cyclic peptide according to the present invention for use in medicine.

According to the present invention this object is solved by providing the cyclic peptide according to the present invention suitable for use as scavenger of methylglyoxal and/or reactive carbonyl species (RCS).

According to the present invention this object is solved by providing the cyclic peptide according to the present invention suitable as antagonist for binding to arginine-containing protein(s), preferably an arginine containing extracellular or intracellular protein, such as low density lipoprotein, Nav1.8, glomerular and tubular proteins of the kidney.

According to the present invention this object is solved by providing the cyclic peptide according to the present invention for use in a method of prevention and/or treatment of a disease caused by or associated with methylglyoxal (MG) and/or reactive carbonyl species (RCS), in particular caused by or associated with elevated MG levels.

According to the present invention this object is solved by providing a pharmaceutical composition comprising
- at least one cyclic peptide according to the present invention,
- optionally a pharmaceutically acceptable carrier and/or excipient.

According to the present invention this object is solved by providing a method for identifying compounds that influence diabetes and its associated complications, in particular diabetes and its associated complications caused by or associated with methylglyoxal and/or reactive carbonyl species (RCS), comprising
(a) providing a compound to be screened,
(b) providing a cyclic peptide according to the present invention,
(c) determining the effect of the compound to be screened of (a) on the development and/or progression of diabetes and its associated complications,
wherein said associated complications comprise diabetic neuropathy (such as pain and/or hyperalgesia), diabetic nephropathy (such as albuminuria and/or lowered eGFR), diabetic retinopathy and endothelial dysfunction.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Methylglyoxal-Scavenging Cyclic Peptide Compounds

As outlined above, the present invention provides cyclic peptide compounds.

A cyclic peptide of the present invention comprises the amino acid sequence of

$Xaa_m\text{-}(Arg)_n\text{-}Glu_o$ wherein Xaa is selected from Lys, ornithine (2,5-diaminopentanoic acid), 2,4-diaminobutanoic acid, 2,3-diaminopropanoic acid,
m is at least 1,
n is selected from 2 to 8,
o is 0 or 1,
and a hydrophobic modification.

The cyclic peptides of the present invention are preferably cyclized via (a) head-to-side chain cyclization, preferably the side chain of the C-terminal Glu,
(b) head-to-tail cyclization,
(c) backbone cyclization,
(d) amide condensation of two amino acid side chains (lactam),
(e) thioether formation,
(f) hydrogen bond formation,
and/or
(g) side chain-to-tail cyclization, In a preferred embodiment, the cyclic peptides of the present invention are cyclized via head-to-side chain cyclization, wherein the head is a lysine (Lys) and the side chain is preferably the side chain of the C-terminal glutamic acid (Glu), i.e. o=1.

Preferably, the hydrophobic modification is an acylation, more preferably
- an acylation with C12 to C22 fatty acids, such as myristoyl (C14), palmitoyl (C16) or stearoyl (C18), more preferably myristoyl (C14),
or
- an acylation with C12 to C22 dicarboxylic acids, such as tetradecanedioic acid (C14), hexadecanedioic acid (C16) (Hdd), octadecanedioic acid (C18), more preferably hexadecanedioic acid (C16),
or
- an acylation with a fatty acid containing phenyl group, such as 4-(p-iodophenyl)butyric acid.

Preferably, the hydrophobic modification is attached to the side chain of an amino acid, preferably of Xaa, optionally via a linker.

In a preferred embodiment, the hydrophobic modification is
- an acylation with a fatty acid, preferably myristoyl, which is attached via the side chain of $Xaa_m$, wherein Xaa=Lys and m=1.

In a preferred embodiment, the hydrophobic modification is
- an acylation with a dicarboxylic acid, preferably hexadecanedioic acid (C16) (Hdd), which is attached via a linker to the side chain of $Xaa_m$, wherein Xaa=Lys and m=1 and wherein the linker is an amino acid, preferably D-Glu.

In a preferred embodiment the cyclic peptide is represented by the following formula

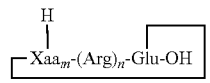

wherein
Xaa is Lys, ornithine (2,5-diaminopentanoic acid), 2,4-diaminobutanoic acid, 2,3-diaminopropanoic acid, preferably Lys,
m is at least 1,
n is 4,
H is the hydrophobic modification,
preferably the cyclic peptide is

wherein H is preferably selected from myristoyl or linker-hexadecanedioic acid, wherein the linker is D-Glu.

The cyclic peptide according to the present invention is preferably selected from
     (I)
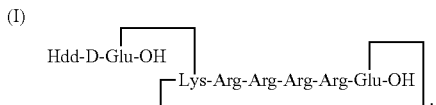     (II)
.
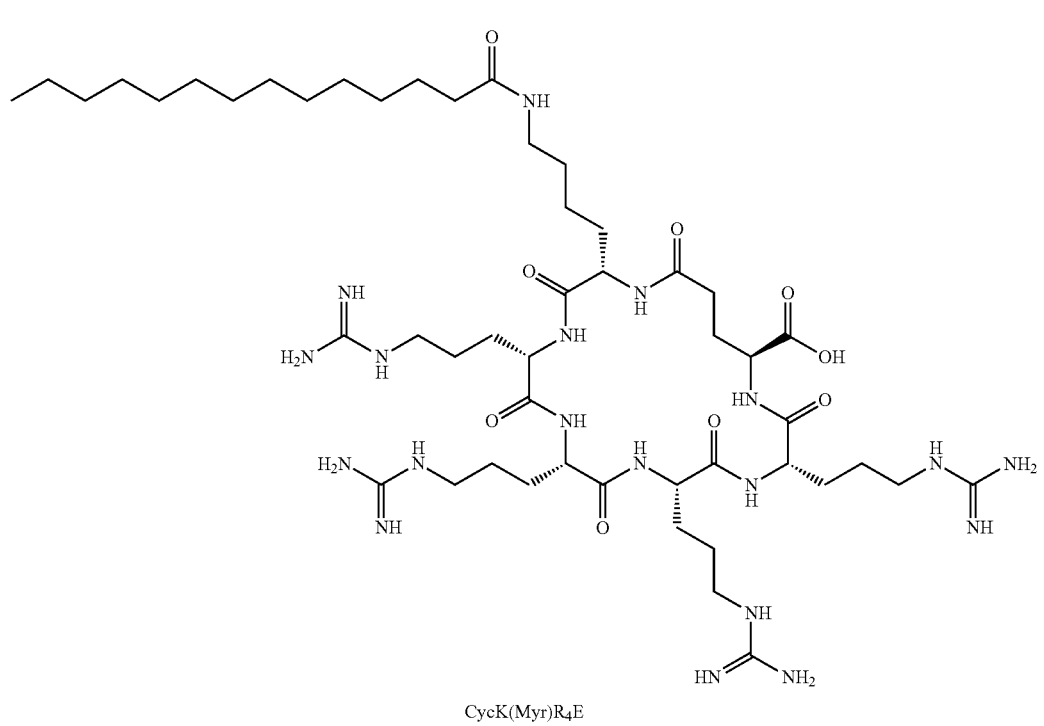     (I)
CycK(Myr)R4E
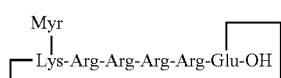
CycK(Myr)R4E -continued

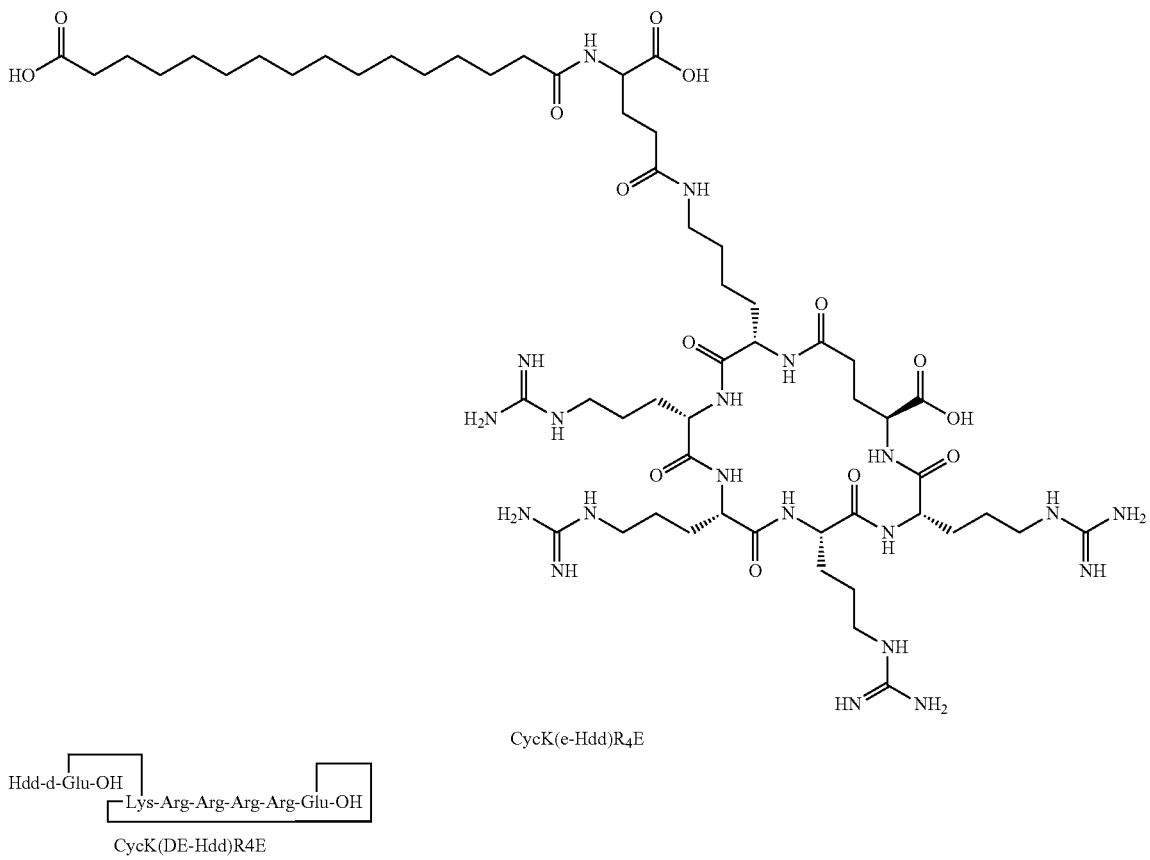

(II)

CycK(e-Hdd)R$_4$E

Hdd-d-Glu-OH
Lys-Arg-Arg-Arg-Arg-Glu-OH

CycK(DE-Hdd)R4E

Within this specification, this peptide is either denoted as "CycK(D-E-Hdd)R$_4$E" or "CycK(DE-Hdd)R$_4$E" or "CycK(-Hdd)R$_4$E". All refer to the same peptide.

In embodiments of this invention the cyclic peptides can comprise a further moiety or moieties,
such as
drug(s) or their respective prodrug(s);
tag(s);
label(s), such as fluorescent dye(s), radioisotope(s) and contrast agent(s);
recombinant virus(s) or derivative(s) thereof;
carrier or depot(s) for drug(s), prodrug(s) or label(s);
immunogenic epitope(s);
hormones;
inhibitor(s);
toxins.
preferably covalently attached, such as via a linker, spacer and/or anchor group(s), e.g. a cleavable linker.

In a preferred embodiment, the cyclic peptides according to the present invention inhibit the binding of methylglyoxal (MG) and/or reactive carbonyl species (RCS) to an arginine- or lysine-containing protein.

An arginine- or lysine-containing protein can be an arginine-containing cellular protein, such as a sodium ion channel, e.g. the sodium ion channel Na(v)1.8.

The range of proteins affected includes but is not limited to the renal glomeruli (extra- and intracellular), renal tubules (extra- and intracellular), low density lipoproteins (extracellular in plasma contributing to atherosclerosis) as well as sodium channels, such as the sodium channel Nav 1.8.

A cyclic peptide compound according to the present invention is preferably capable to
bind and scavenge methylglyoxal and other RCS in vivo and in vitro,
and/or
antagonize and/or compete with MG and other RCS for binding to proteins, preferably arginine- or lysine-containing extracellular proteins, such as the low density lipoprotein,
and/or
prevent the modification of proteins, preferably arginine- or lysine-containing extracellular proteins, such as the low density lipoprotein by MG and other RCS,
and/or
antagonize and/or compete with MG and RCS for binding to proteins, preferably arginine- or lysine containing proteins of the glomerulus and tubule of the kidney.
and/or
prevent the modification of proteins, preferably arginine- or lysine-containing extracellular proteins, proteins of the glomerulus and tubule of the kidney.
and/or
antagonize and/or compete with MG and other RCS for binding to proteins, preferably arginine- or lysine-containing (cellular) proteins, such as the sodium ion channel Na(v) 1.8,
and/or
prevent the modification of proteins, preferably arginine- or lysine-containing (cellular) proteins, such as the sodium ion channel Na(v)1.8, by MG and other RCS,
and/or inhibit and/or prevent the formation of advanced glycation endproducts (AGEs) by methylglyoxal and other RCS.

The "scavenging potential" of a cyclic peptide compound as used herein can be viewed as the amount of methylglyoxal which can react with a cyclic peptide compound of the invention and therefore be the effective amount of methylglyoxal or similarly acting reactive metabolites (such as reactive carbonyl species (RCS)) which are removed from binding to arginine- or lysine-containing (intra- and extracellular) proteins at any situation in which methylglyoxal or similarly acting reactive metabolites (such as reactive carbonyl species (RCS)) are elevated.

Use of the Cyclic Peptide Compounds as Methylglyoxal Scavenger and/or Antagonist As outlined above, the present invention provides the cyclic peptide compounds of the present invention as scavengers of methylglyoxal and/or reactive carbonyl species (RCS).

As outlined above, the present invention provides the cyclic peptide compounds of the present invention as antagonists of methylglyoxal for binding to an arginine-containing protein(s), preferably an arginine containing extracellular protein, preferably low density lipoprotein.

As outlined above, an arginine-containing protein includes but is not limited to the renal glomeruli (extra- and intracellular), renal tubules (extra- and intracellular), low density lipoproteins (extracellular in plasma contributing to atherosclerosis) as well as sodium channels, such as the sodium channel Nav 1.8.

Preferably, the cyclic peptides according to the present invention are suitable for use as antagonist for binding to arginine-containing protein(s), preferably an arginine containing extracellular or intracellular protein, such as
low density lipoprotein,
Nav1.8,
glomerular and tubular proteins of the kidney.

In the context of this invention, the term "scavenger" of methylglyoxal and/or "scavenging" methylglyoxal, therefore refers to the potential of the cyclic peptide compound to prevent the interaction of methylglyoxal (or similarly acting reactive metabolites, such as reactive carbonyl species (RCS)) with protein residues, specifically arginine residues or also lysine residues, in proteins, on and/or in macromolecular protein structures and physiological proteins, as outlined above, in vitro as well as in vivo.

The cyclic peptide compounds of the invention are suitable as in vitro as well as in vivo scavengers of methylglyoxal and/or reactive carbonyl species (RCS).

Pharmaceutical Compositions and Medical Applications

As outlined above, the present invention provides a pharmaceutical composition comprising at least one compound as defined herein, preferably at least one cyclic peptide as defined herein, and optionally a pharmaceutically acceptable carrier and/or excipient.

The pharmaceutical compositions according to the present invention are very well suited for all the uses and methods described herein.

A "pharmaceutically acceptable carrier or excipient" refers to any vehicle wherein or with which the pharmaceutical compositions according to the invention may be formulated. It includes a saline solution such as phosphate buffer saline. In general, a diluent or carrier is selected based upon the mode and route of administration, and standard pharmaceutical practice.

As outlined above, the present invention further provides the first medical use of the cyclic peptide compounds of this invention.

Thus, the cyclic peptide compounds of this invention are suitable and, thus, provided for the diagnosis, prevention and/or treatment of diseases.

As outlined above, the present invention further provides the cyclic peptide compounds of this invention and/or respective pharmaceutical composition(s) of this invention for the diagnosis, prevention and/or treatment of certain diseases.

In particular, the cyclic peptide compounds of this invention and/or respective pharmaceutical composition(s) of this invention are suitable for the prevention and/or treatment of a disease caused by or associated with methylglyoxal (MG) and/or reactive carbonyl species (RCS).

Said "disease caused by or associated with methylglyoxal (MG) and/or reactive carbonyl species (RCS)" is in particular caused by or associated with elevated MG levels Said disease is preferably selected from:
diabetes and its associated complications,
  wherein said associated complications comprise
    diabetic neuropathy (such as pain and/or hyperalgesia),
    diabetic nephropathy (such as albuminuria and/or lowered eGFR),
    diabetic retinopathy, and
    endothelial dysfunction,
cardiovascular disease,
  in particular atherosclerosis,
obesity,
Alzheimers disease, amyotrophic lateral sclerosis, cataractogenesis, chronic renal failure and chronic or acute Uraemia, cystic fibrosis, dementia with Lewy bodies, ischaemia-reperfusion, pre-eclampsia, psoriasis, rheumatoid arthritis and juvenile chronic arthritis, severe sepsis, systemic amyloidosis and Parkinson's disease.

"Pain" (and/or "hyperalgesia") as used herein refers preferably to pain (and/or hyperalgesia) and/or a disease/condition associated with pain and/or hyperalgesia caused by or associated with methylglyoxal and/or reactive carbonyl species (RCS).

The inventors have found that cyclic peptide compounds, which inhibit or antagonize the binding of methylglyoxal (MG) and/or reactive carbonyl species (RCS) to an arginine (or lysine)-containing protein, preferably an arginine (or lysine)-containing cellular protein, such as a sodium ion channel, e.g. the sodium ion channel Na(v)1.8 (the methylglyoxal-scavenging compounds with the characteristics described herein), are suitable for a novel and specific treatment/therapy for pain and/or hyperalgesia, wherein the components causing the pain/hyperalgesia or are associated therewith (namely methylglyoxal (MG) and/or reactive carbonyl species (RCS)) are targeted.

Similar to the prevention of pain via MG scavenging MG can also cause atherosclerosis and as such cardiovascular disease. MG modified low density lipoproteins display an increased atherogenicity while the binding to the LDL receptor is decreased, thus affecting the clearance. An involvement of MG has also been demonstrated in diabetic nephropathy where MG levels are elevated while the modification of proteins with MG are a strong independent predictor of diabetic nephropathy. Furthermore, a decrease in the MG detoxifying enzyme mimicked the development of diabetic nephropathy with increased levels MG-protein adducts, albuminuria and expansion of the mesangial matrix.

In a preferred embodiment the cyclic peptide or the pharmaceutical composition(s) of the invention are used for the manufacture of a medicament for the prevention and/or treatment of atherosclerosis and/or cardiovascular disease caused by or associated with methylglyoxal and/or reactive carbonyl species (RCS).

In a preferred embodiment the cyclic peptide or the pharmaceutical composition(s) of the invention are used for the manufacture of a medicament for the prevention and/or treatment of diabetic nephropathy caused by or associated with methylglyoxal and/or reactive carbonyl species (RCS).

In a preferred embodiment the cyclic peptide or the pharmaceutical composition(s) of the invention are used for the manufacture of a medicament for the prevention and/or treatment of pain and/or hyperalgesia, in particular pain and/or hyperalgesia caused by or associated with methylglyoxal and/or reactive carbonyl species (RCS).

In a preferred embodiment, the cyclic peptide compounds are provided as analgesic.

The pain and/or hyperalgesia to be prevented and/or treated is associated with and/or occurs during a disease, wherein said disease is selected from Alzheimers disease, amyotrophic lateral sclerosis, cataractogenesis, chronic renal failure and chronic and acute Uraemia, cystic fibrosis, dementia with Lewy bodies, diabetes mellitus and its complications (such as nephropathy, neuropathy and retinopathy), ischaemia-reperfusion, pre-eclampsia, psoriasis, rheumatoid arthritis and juvenile chronic arthritis, severe sepsis, systemic amyloidosis, Parkinson's disease, painful bowel disease, chemotherapy induced pain, critical limb ischemia, hypertension, bone pain, tumor pain.

In diabetes mellitus, neuropathy, which is one of three major complications associated with the diseases, is frequently observed with patients exhibiting one or more types of stimulus-evolved pain, including increased responsiveness to noxious stimuli (hyperalgesia) as well as hyper-responsiveness to normally innocuous stimuli (allodynia). The underlying mechanism of persistent pain diabetic patients remains poorly understood and as such there are little or no effective therapeutic treatments which can either delay or prevent the onset of symptoms.

The formation of methylglyoxal and related reactive carbonyl species (RCS) is closely linked to the rate of glycolysis and the presence of glycolytic intermediates. Hence, in conditions where there is increased glycolytic flux and an increased dependence on glycolysis for energy, the rate of methylglyoxal and RCS formation will also be increased. This has been shown to be the case in patients with diabetes mellitus, where complications such as nephropathy, neuropathy and retinopathy have been linked to increases in cellular levels of advanced glycation endproducts (AGEs). While diabetes has been the main area of research, new evidence is now emerging of the pivot role that RCS, in particularly methylglyoxal, plays in the progression and severity of various diseases, such as, but not limited to cardiovascular disease.

For example, methylglyoxal modification of Nav1.8 facilitates nociceptive neuron firing and causes metabolic hyperalgesia:

Small fiber distal polyneuropathy causes persistent hyperalgesia and pain in 10% of people with diabetes. Metabolic hyperalgesia is based on the reactive glycolytic metabolite methylglyoxal (MG). MG exceeding plasma levels of 600 nM discriminates between diabetic patients with and without pain, evokes thermal hyperalgesia in mice and induces CGRP release in skin flaps. Cultured sensory neurons treated with MG exhibit intense MG-modifications of arginine residues in the sodium-channel $Na_v1.8$ and increased electrical excitability and membrane resistance. MG effects on action potential generators facilitate firing in nociceptive neurons but inhibit neurons of the autonomic nervous system lacking $Na_v1.8$ expression. The understanding of metabolic driven pain is useful for therapeutic interventions, since an MG binding peptide is able to reduce hyperalgesia in experimental diabetes, thus providing the first pathogenetically based treatment option for painful diabetic neuropathy.

There exists a concept of neuronal dysfunction in certain metabolic diseases. The major insight is the identification (by the inventors) of a key role for local accumulation of the reactive metabolite MG, which by posttranslational modification of the sensory neuronal sodium channel $Na_v1.8$ enhances the excitability and blocks other ion channels including $Na_v1.7$. The concept of metabolic hyperalgesia appears independent of structural changes in the nerve but rather dependent on the molecular interaction of MG with arginine and lysine residues within critical regions of $Na_v1.8$. This observation is compatible with the threshold of about 600 nM MG required to affect neuronal function which was observed in men, mice and peripheral nerve endings. There are several possibilities by which the required MG threshold can be reached. One is the increased metabolic flux of glucose in diabetes through either glycolysis or the pentose phosphate pathway. Under non-diabetic conditions, the incidental amount of MG generated is detoxified by protective enzymes, particularly the glyoxalase system. Other pathological states leading to increased generation of MG are disorders in which acetone and other ketone bodies accumulate, such as uremia, or conditions such as oxidative stress during re-perfusion in which lipid peroxidation occurs.

Route of Administration

Preferably, the route of administration of the cyclic peptide compounds or pharmaceutical compositions of the present invention is selected from subcutaneous, intravenous, oral, nasal, intramuscular, transdermal, inhalative, by suppository.

A preferred embodiment for nasal administration or application is as an inhalant spray, which would be advantageous for cyclic peptide compound(s), as it would not only allow for faster acting effect, but also limit degradation which may result from oral administration, either from nausea or degradation in the gut or liver.

Therapeutically Effective Amount

The cyclic peptide compounds or the pharmaceutical compositions of the invention are provided such that they comprise a therapeutically effective amount of said cyclic peptide compound(s) or of said pharmaceutical composition(s).

A "therapeutically effective amount" of a cyclic peptide compound or a pharmaceutical composition of this invention refers to the amount that is sufficient to induce a reduction of ≥50% in clinical symptoms of the treated disease. Within the context of this invention, this includes but is not exclusively limited, to a reduction of ≥50% in the levels of pain within a patient as determined by the normal clinical parameters.

A preferred therapeutically effective amount is in the range of 10 µg to 1 mg per kg body weight, preferably 10 µg to 100 µg.

The preferred therapeutically effective amount depends on the respective application and desired outcome of inhibition, treatment or prevention.

The skilled artisan will be able to determine suitable therapeutically effective amounts.

Screening Method

The invention further provides a screening method, in particular a method for identifying/screening compounds that influence diabetes and its associated complications, in particular diabetes and its associated complications caused by or associated with methylglyoxal and/or reactive carbonyl species (RCS).

Said method preferably comprises (a) providing a compound to be screened, (b) providing a cyclic peptide compound according to the present invention (as defined herein), (c) determining the effect of the compound to be screened of (a) on the development and/or progression of diabetes and its associated complications, wherein said associated complications comprise diabetic neuropathy (such as pain and/or hyperalgesia), diabetic nephropathy (such as albuminuria and/or lowered eGFR), diabetic retinopathy and endothelial dysfunction.

The skilled artisan will be able to determine and apply a suitable test model.

Such a test model might comprise one or more of the following an arginine-containing protein, and/or methylglyoxal and/or reactive carbonyl species (RCS).

Suitable arginine-containing protein(s) are plasma proteins, preferably albumin, and/or low density lipoprotein and/or proteins of the extracellular matrix and/or sodium channel Na(v) 1.8.

PREFERRED EMBODIMENTS

Abstract: The reactive metabolite methylglyoxal (MG) has been identified as mediator of pain. Scavenging of free MG and the prevention of MG-derived post-translational modifications may provide a useful therapeutic treatment. An arginine-rich, fatty acid coupled, cyclic peptide (CycK (Myr)R4E) with high proteolytic stability and prolonged circulation was developed by the inventors for the scavenging of MG. Herein it is shown to reduce the formation of albumin-MG adducts in vitro and to prevent MG-induced hyperalgesia by reducing plasma MG levels through the formation of peptide-MG adducts in vivo. CycK(Myr)R4E therefore presents a promising option for the treatment pain and other diseases which are associated with high MG levels.

Herein, we report in vitro and in vivo data on newly developed arginine-based MG scavenging peptides with such characteristics. This opens up new options for the treatment of pain and other diabetic complications associated with excessive MG formation.

The main sites of MG modification of proteins are arginine residues and the AGE methylglyoxal-hydroimidazolone 1 (MG-H1) (FIG. 1 A-C) is the major resulting MG-arginine adduct. In previous work we reported on a 40 amino acid long MG scavenger peptide (FIG. 1 D: GERP$_{10}$ (SEQ ID NO. 18)) (Bierhaus et al., 2012; see also WO 2010/136182). Here, we demonstrate that increasing the relative arginine content had the greatest improvement on MG scavenging activity (Table 1) of peptides.

TABLE 1

Comparison of MG scavenging kinetics of pentapeptides AXRAA.

| Peptide | MG t$_{1/2}$ [h] | 95% CI | SEQ ID NO. |
|---|---|---|---|
| A<u>R</u>RAA | 3.69 | 2.89-5.13 | 2 |
| A<u>K</u>RAA | 4.02 | 3.33-5.08 | 3 |
| A<u>C</u>RAA | 5.30 | 4.32-6.86 | 4 |
| A<u>V</u>RAA | 9.03 | 6.98-12.78 | 5 |
| A<u>Q</u>RAA | 9.42 | 8.55-15.77 | 6 |
| A<u>Y</u>RAA | 9.68 | 8.54-11.19 | 7 |
| A<u>W</u>RAA | 9.83 | 8.52-11.61 | 8 |
| A<u>A</u>RAA | 10.24 | 8.80-12.24 | 9 |
| A<u>N</u>RAA | 10.29 | 8.69-12.61 | 10 |
| A<u>F</u>RAA | 10.39 | 8.90-12.47 | 11 |
| A<u>M</u>RAA | 10.56 | 9.47-11.93 | 12 |
| A<u>L</u>RAA | 10.76 | 8.62-14.32 | 13 |
| A<u>H</u>RAA | 10.95 | 9.25-13.41 | 14 |
| A<u>S</u>RAA | 11.06 | 8.52-11.61 | 15 |
| A<u>D</u>RAA | 11.62 | 8.10-20.56 | 16 |
| A<u>E</u>RAA | 12.59 | 11.00-14.72 | 17 |

Therefore, an arginine-rich peptide is best suited as MG scavenger while cyclisation is known to improve the proteolytic stability (Li et al., 2002). The coupling of fatty acids such as myristic acid prolongs the half-life of drugs through non-covalent interaction with albumin (Jonassen et al., 2012; Kontermann 2011). Consequently, a cyclic arginine-rich peptide (FIG. 1 E: CycR$_4$E) as well as a myristic acid (Myr) coupled derivative (FIGS. 1 F and G: CycK(Myr) R$_4$E) were synthesized with the aim to extend the half-life.

Albumin is the most abundant plasma protein and contains 24 arginine residues 21 of which are capable of participating in the glycation reaction leading to irreversible protein modifications (Anguizola et al., 2013). We determined whether MG scavengers are capable of preventing the formation of albumin-MG-H1 modifications. The activity of the novel peptide scavengers was tested in parallel to several small molecules (structures shown in FIG. 2 A), previously described to bind MG or other reactive carbonyls. Amongst the latter were the endogenous molecules carnosine (Car), creatine (Cre) and the vitamer pyridoxamine (Pyr), the investigational drugs aminoguanidine (Agd) and alagebrium (Ala) and the widely prescribed anti-diabetic drug metformin (Met) (Dhar et al., 2010; Kinsky et al., 2016; Lobner et al., 2015; Lo et al., 1994; Nagaraj et al., 2002; Vistoli et al., 2009). The scavengers were incubated with MG in the presence of human serum albumin (HSA). HSA was subsequently analyzed for MG-H1 content by LC-MS following serial enzymatic digestion (Thornalley et al., 2003). The kinetics of MG scavenging were determined in parallel (Table 2). The peptide scavengers, CycK(Myr)R$_4$E, CycR$_4$E and GERP$_{10}$ (SEQ ID NO. 18) were similar to alagebrium in terms of the prevention of HSA-MG-H1 formation (FIG. 2 B), and was unaffected by the presence of myristic acid. Agd had faster scavenging kinetics (t$_{1/2}$=0.2 h for Agd vs. 1.3 h-3.2 h for peptide scavengers) and tended to be more efficient at preventing HSA-MG-H1 adduct formation than the peptide scavengers. Despite this feature clinical trials of this compound had been stopped due to side effects (Forbes et al., 2013). Metformin and pyridoxamine were slow MG scavengers which did not significantly prevent HSA-MG-H1 formation. However, even the slow MG scavenging kinetics of metformin could provide a therapeutic effect. In support of this, metformin reduces systemic MG levels and recently, a MG-metformin adduct was detected in the urine at concentrations up to 4 µM (Kinsky et al., 2016; Beisswenger et al., 1999). Similar to metformin, the endogenous molecule creatine has been described as a MG scavenger and the MG creatine adduct was found in the urine (Lobner et al., 2015). Creatine was the fastest of the endogenous MG scavengers tested but only a trend for the prevention of HSA-MG-H1 formation in vitro was observed. The dipeptide carnosine neither scavenged MG nor did it prevent HSA-MG-H1 formation. This is in contrast to the scavenging effect of carnosine on the reactive aldehyde 4-hydroxytrans-2-nonenal (Vistoli et al., 2009).

TABLE 2

MG scavenging kinetics of MG scavenger peptides and small molecule carbonyl scavengers.

| Peptide | MG $t_{1/2}$ [h] | 95% CI |
| --- | --- | --- |
| Agd | 0.24 | 0.15-0.58 |
| Ala | 0.77 | 0.68-0.88 |
| CycK(e-Hdd)$R_4$E | 1.1 | 1.00-1.30 |
| $GERP_{10}$ | 1.36 | 1.13-1.70 |
| CycK$R_4$E | 1.95 | 1.66-2.37 |
| CycK(Myr)$R_4$E | 3.28 | 2.8-3.96 |
| Cre | 7.36 | 6.24-8.96 |
| Met | 17.29 | 14.54-21.33 |
| Pyr | 20.90 | 18.65-23.77 |
| Car | 138.1 | 103.5-207.6 |

MG content was measured after co-incubation of scavenger (400 μM) and MG (200 μM) at time points 0 h, 1 h, 4 h, 8 h, 24 h and 48 h in triplicates and half-life of MG was determined by non-linear regression analysis. Half-life and the 95% confidence interval of the half-life are given.

A long circulatory time is mandatory for the peptide scavenger to bind MG and must therefore be stable towards proteolysis. This was achieved by cyclisation (FIG. 5). Using positron emission tomography, the pharmacokinetics of the myristic acid coupled CycK(Myr)$R_4$E peptide was compared to uncoupled $GERP_{10}$ (SEQ ID NO. 18) and CycK$R_4$E in mice. In brief, DOTA derivatives of the peptides were labeled with $^{68}$Ga, administered i.v. to mice and distribution followed by PET. Fatty acid free K(DOTA)$GERP_{10}$ (SEQ ID NO. 19) (FIG. 2 C) as well as CycK(DOTA)$R_4$E (FIG. 2 D) were excreted almost completely within 20 min. The myristic acid coupled peptide CycK(DOTA)K(Myr)$R_4$E (FIG. 2 E) circulated for more than 2 h due to its interaction with albumin (see FIGS. 6 A and B for quantification).

Based upon the pharmacokinetics the CycK(Myr)$R_4$E peptide was subsequently tested for MG scavenging activity in mice. Mice were injected with the peptide i.p. (0.25 mg/mouse) 30 min prior to injection with MG i.v. (5 μg/g body weight). Plasma was collected via the mandibular vein 30 min after MG injection and analyzed for MG levels by LC-MS/MS. Control mice had MG plasma levels of approximately 150 mmol whereas MG injection resulted in increased MG plasma levels which was lowered by treatment with CycK(Myr)$R_4$E (FIG. 3 A).

Elevated MG plasma levels are associated with hyperalgesia, an increased sensitivity towards pain, in diabetic patients while injection of MG produces hyperalgesia in mice via modification of proteins (Bierhaus et al., 2012; Eberhardt et al., 2012). To assess whether decreased MG levels upon peptide treatment were associated with an improvement of hyperalgesia mice were treated as described for the determination of MG plasma levels. The effect of the peptide on MG induced hyperalgesia was assessed by hotplate assay 3 h after MG injection. Values were normalized for the average response time of the control animals (20.75 s+/−0.60 s). Mice which received MG displayed hyperalgesia whilst treatment with the MG-scavenging peptide CycK(Myr)$R_4$E prior to MG injection resulted in an almost complete normalization of hyperalgesia (FIG. 3B).

MG-H1 represents the most frequently formed arginine-MG adduct. Modification of CycK(Myr)$R_4$E with MG is therefore likely to result in an MG-H1 modified peptide. To establish whether this was the case, the plasma from the mice treated with the peptide and MG was analyzed for the presence of the MG-H1 modified peptide. To achieve this, four peptides with one MG-H1 replacing each of the four arginine positions were synthesized as standards using Fmoc-MG-H1 (Dod)-OH (Wang et al., 2012). The respective MG-H1 modified peptides were subsequently detected by LC-MS/MS. MG-H1 modified peptides (MG-adducts #1-3) were detectable in mice which received the peptide prior to MG injection (FIG. 3 C) showing that the peptide scavenges MG in vivo. Scavenging was also observed in plasma donated from a patient with type 2 diabetes where MG-adduct #4 was observed in addition (FIG. 3 D).

It was previously shown that AGE modification of proteins triggers their uptake by the kidneys and the liver (Nagai et al., 2007). The resulting increased proteolytic load may contribute to the development of diabetic complications and other age related diseases (Brings et al., 2015; Uchiki et al., 2012). A DOTA conjugated derivative of a MG-H1 modified scavenger peptide was synthesized to determine whether a potentially pathogenic elevated uptake of the MG-H1 modified peptide into the kidney and liver can be observed. The MG-H1 modified scavenger peptide was compared to unmodified scavenger peptide by PET after labeling with $^{68}$Ga. PET analysis was carried out in triplicates and the standardized uptake values (SUV) calculated. The level of the MG-H1 modified peptide was higher in the bladder (FIG. 4 A) while levels in the kidney (FIG. 4 B) and the liver (FIG. 4 C) were lower when compared to the unmodified peptide. The levels in the muscle (FIG. 4 D) and heart (FIG. 4 E) were similar for both peptides. Representative PET images are presented in FIG. 4 F for the unmodified peptide and FIG. 4 G for the modified peptide. This reveals that the modified peptide is readily excreted via the kidney and the bladder. Consequently, the potentially pathogenic MG-H1 modified peptide did not accumulate in the excretory organs.

In summary, a small peptide, CycK(Myr)$R_4$E, has been developed, which efficiently scavenges MG and prevents the formation of HSA-MG-H1 adducts in vitro. The peptide significantly reduces MG plasma levels and normalizes MG-induced hyperalgesia in mice. PET analysis revealed that the MG-modified peptide is excreted via the kidneys. The cyclisation of the peptide contributes to its increased plasma stability whilst the attachment of myristic acid improves its half-life through non-covalent binding of albumin. The pharmacokinetic and pharmacodynamics properties of CycK(Myr)$R_4$E therefore make it a promising candidate for the treatment of diabetic neuropathy and other diabetic complications which are associated with increased plasma levels of the reactive metabolite MG.

A peptide with an alternative fatty acid moiety namely hexadecanedioic acid which was coupled via a D-Glutamic acid linker was synthesized (See FIG. 7 for structure and comparison with CycK(Myr)$R_4$E).

Comparison of biodistribution of DOTA coupled peptides CycK(DOTA)K(e-Hdd)$R_4$E and CycK(DOTA)K(Myr)$R_4$E as well as the fatty acid free peptide CycK(DOTA)$R_4$E was carried out by positron emission tomography with the following results. Both fatty acid modified peptides (see FIG. 8) remain in the animals for over 2 h whereas the fatty acid free peptide is excreted almost completely after 20 min (FIG. 8; only kidney and bladder show signal starting from 20-40 min). One difference between the Hdd and the Myr coupled peptides is that the former appears in the bladder without accumulation in the kidneys whereas the latter shows a strong accumulation in the kidneys prior to excretion through the bladder. Such an accumulation in the kidneys could lead to side effects so that the Hdd coupled peptide is favourable in that respect.

Cyclic peptides were tested without fatty acid modification (CycR$_4$E), with myristic acid modification (CycK(Myr)R$_4$E) as well as with a hexadecanedioic acid modification via a D-glutamic acid linker (CycK(e-Hdd)R$_4$E. All four peptides significantly prevented modification of HSA with MG-H1 (FIG. 9).

It can be concluded that the Hdd coupled peptide have certain advantages over the Myr coupled peptide due to a lower accumulation in the kidneys and a better water solubility (due to the two free carboxy groups) while retaining the favorable MG scavenging kinetics and pharmacokinetics.

CycK(Myr)R$_4$E displays significant hemolysis at concentrations over 50 μM while CycK(e-Hdd)R$_4$E does not cause hemolysis even at high concentrations (FIG. 10).

CycK(e-Hdd)R$_4$E protects from MG induced toxicity. A treatment with said peptide has an ameliorative effect and viability is at 75% (FIG. 11). Furthermore, the half-life of (unmodified) CycK(e-Hdd)R$_4$E was determined to be approximately 8 h when tested after one ip injection (into mice using LC MS) (FIG. 12).

The following examples and drawings illustrate the present invention without, however, limiting the same thereto.

BRIEF DESCRIPTION OF THE DRAWINGS

FIG. 4. Biodistribution of unmodified vs. MG modified scavenger peptide.
Mice were injected with CycK(DOTA)K(Myr)R$_4$E or its MG modified derivative CycK(DOTA)K(Myr)MG-H1$_4$E and analyzed by PET. Standardized uptake values (SUV) for bladder (A), kidneys (B), liver (C), muscle (D) and heart (E) are given. Representative PET images are shown for CycK(DOTA)K(Myr)R$_4$E (F) and CycK(DOTA)K(Myr)MGH1$_4$E (G). Area under the curve of SUV's was compared by Student's t-test; * p<0.05 and **** p<0.0001.

The effect of the peptide CycK(e-Hdd)R$_4$E on MG induced toxicity was tested in murine cardiac endothelial cells. Cells were treated with 4 mM MG or 4 mM MG and 1 mM of the peptide CycK(e-Hdd)R$_4$E. Amount of viable cells was determined by MTT assay and is expressed as percentage relative to untreated cells. In MG treated wells, only 25% of cells are viable compared to untreated controls. Treatment with the peptide has an ameliorative effect and viability is at 75%.

Figure 1:
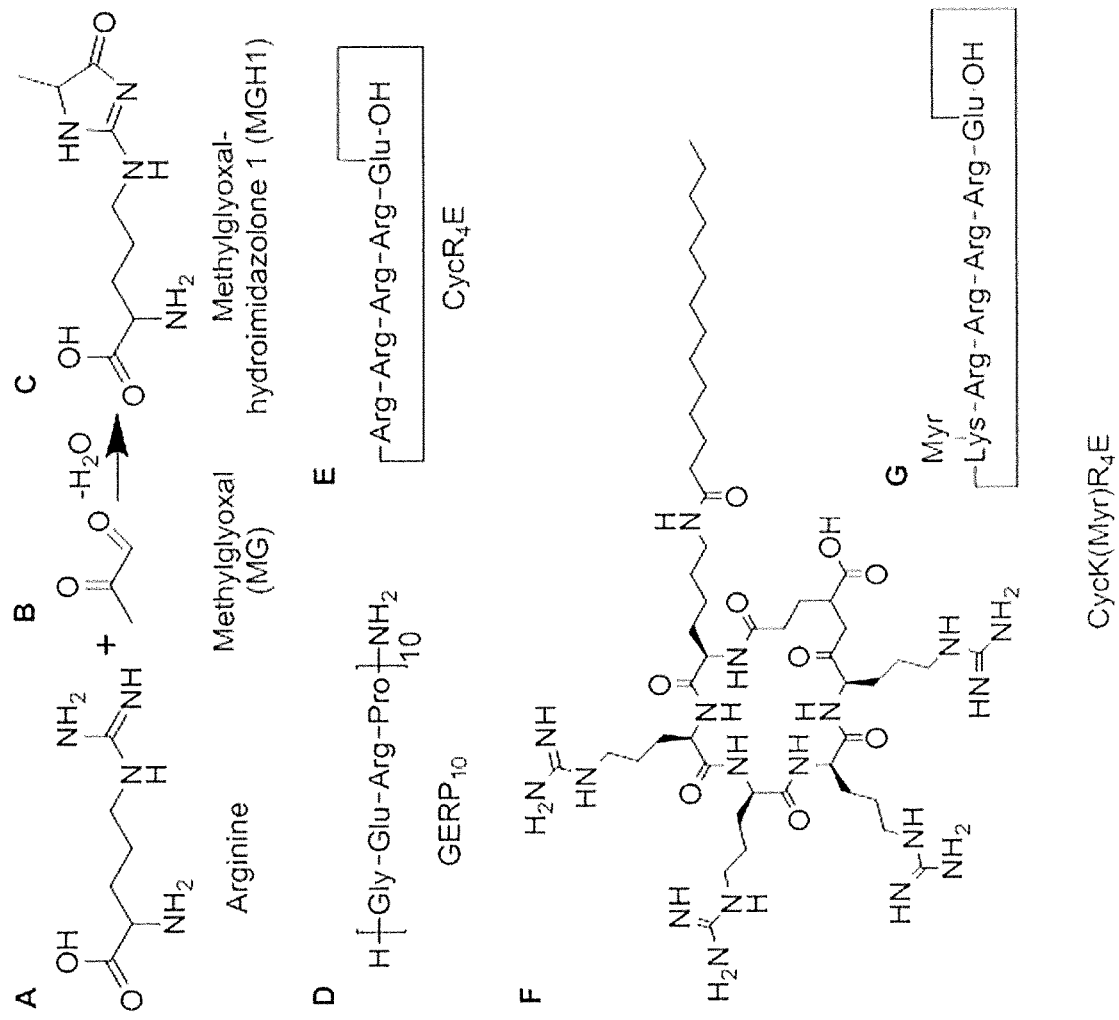
FIG. 1.
Reaction of arginine (A) with MG (B) results in formation of MGH1 (C). Schematic drawings of the peptide scavengers GERP$_{10}$ (SEQ ID NO. 18) (D), CycR$_4$E (E) and structure (F) and schematic drawing (G) for CycK(Myr)R$_4$E.
Figure 2:
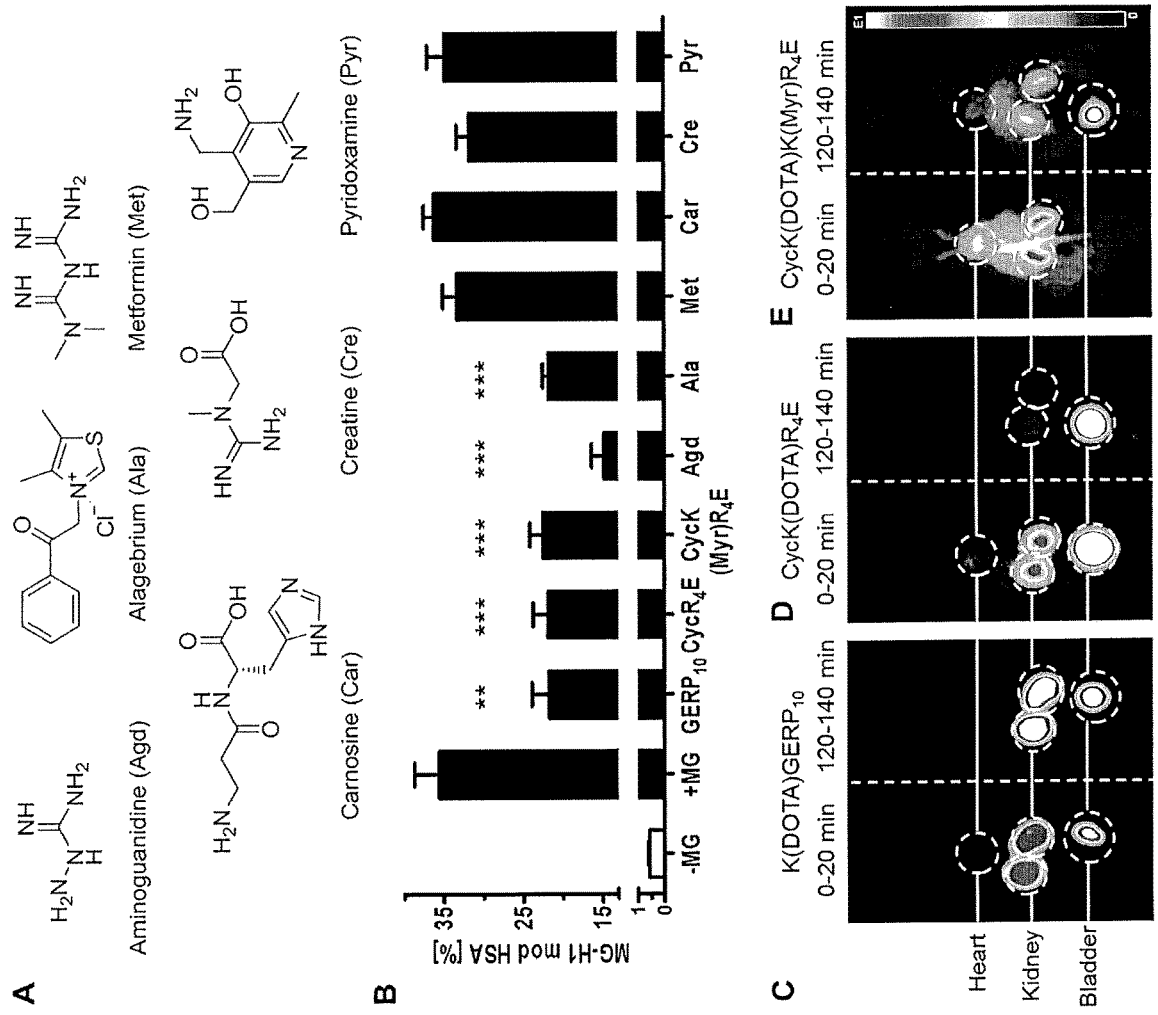
FIG. 2.
Structures of small molecule MG scavengers (A). Competitive scavenging activity of peptides and small molecules in the presence of HSA (B). HSA was incubated without MG (-MG), with MG (+MG) or with MG and the scavenger molecules indicated for 24 h and MG-H1 modified albumin was quantified. PET analysis of the $^{68}$Ga-labelled scavenger peptides K(DOTA)GERP$_{10}$ (C), CycK(DOTA) R$_4$E (D) and CycK(DOTA)K(Myr)R$_4$E (E) in NMRI-mice. Data was analyzed by one-way ANOVA and Tukey-Kramer post-hoc test;  p<0.01 and * p<0.001 vs. +MG.
Figure 3:
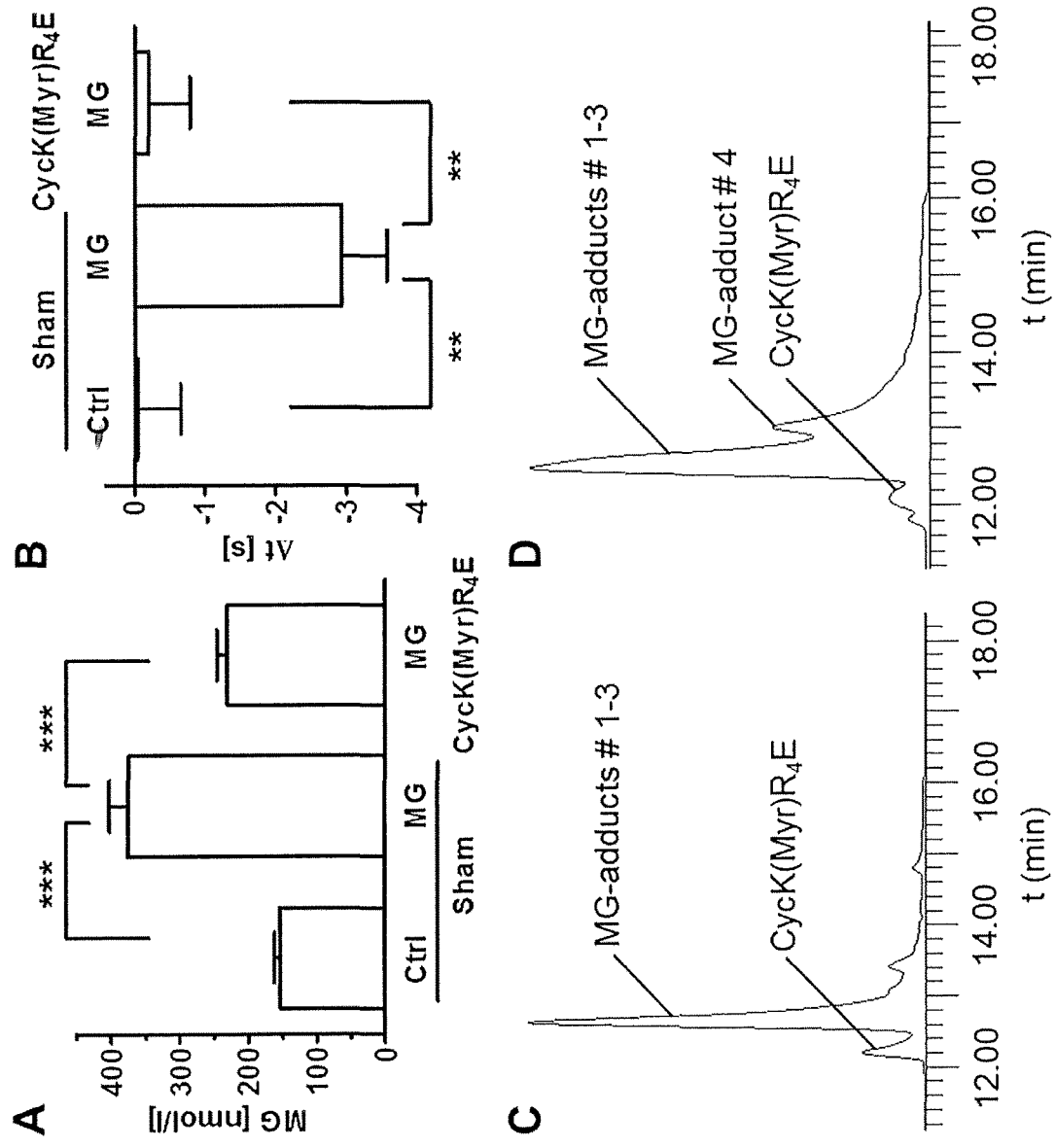
FIG. 3. Efficacy of the MG scavenger CycK(Myr)R$_4$E in mice.
Mice were injected with CycK(Myr)R$_4$E or saline solution (sham) 30 min prior to MG injection or saline injection (ctrl). MG plasma levels were determined 30 min after MG injection (A). The effect of the peptide on pain sensitivity was determined by hot-plate assay 3 h after MG injection (B). The MG-peptide adducts were detected in plasma of mice 3 h after MG injection (C) as well as in plasma from a diabetic patient spiked with the peptide (D). Data was analyzed by one-way ANOVA and Tukey-Kramer post-hoc test;  p<0.01 and * p<0.001.
Figure 5:
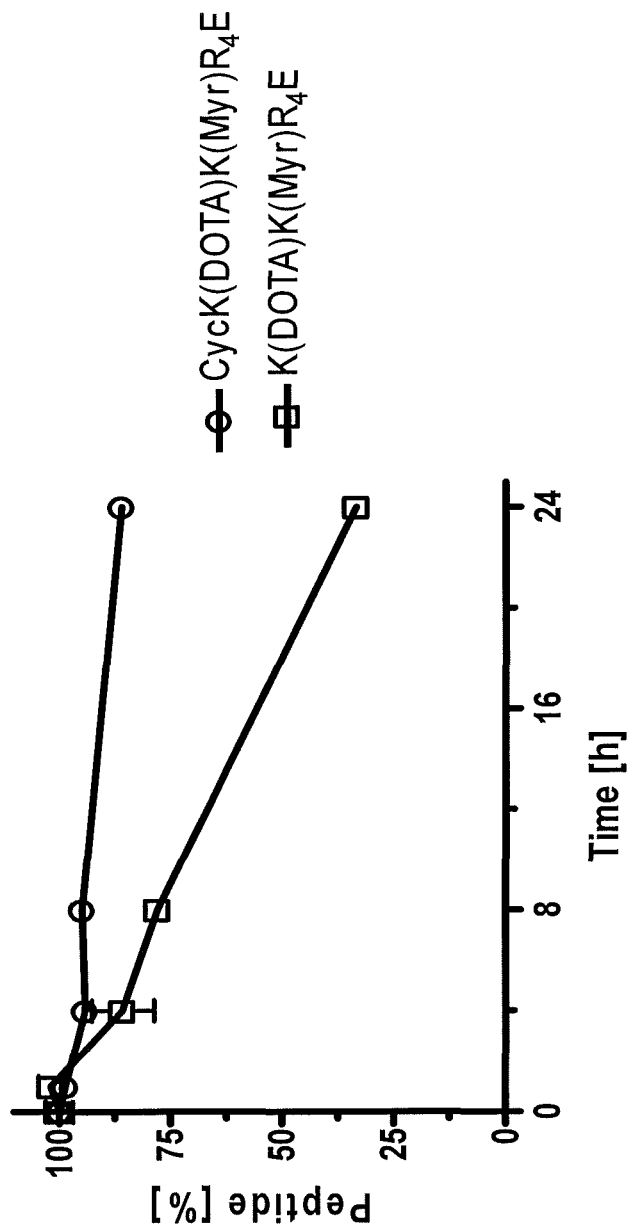
FIG. 5. Serum stability of cyclic and linear peptide.
The cyclic peptide CycK(DOTA)K(Myr)R$_4$E and the linear peptide K(DOTA)K(Myr)R$_4$E were labeled with $^{177}$Lu and incubated with human serum at 37° C. Serum was precipitated at indicated times and supernatant analyzed by HPLC equipped with a radio flow detector. AUC was determined for the peptide at each time point and normalized for the starting time point t=0 h. Cyclic CycK(DOTA)K(Myr)R$_4$E is more stable than the linear counterpart K(DOTA)K(Myr)R$_4$E with 86.16% vs. 33.4% of the peptide remaining after 24 h, respectively.
Figure 6:
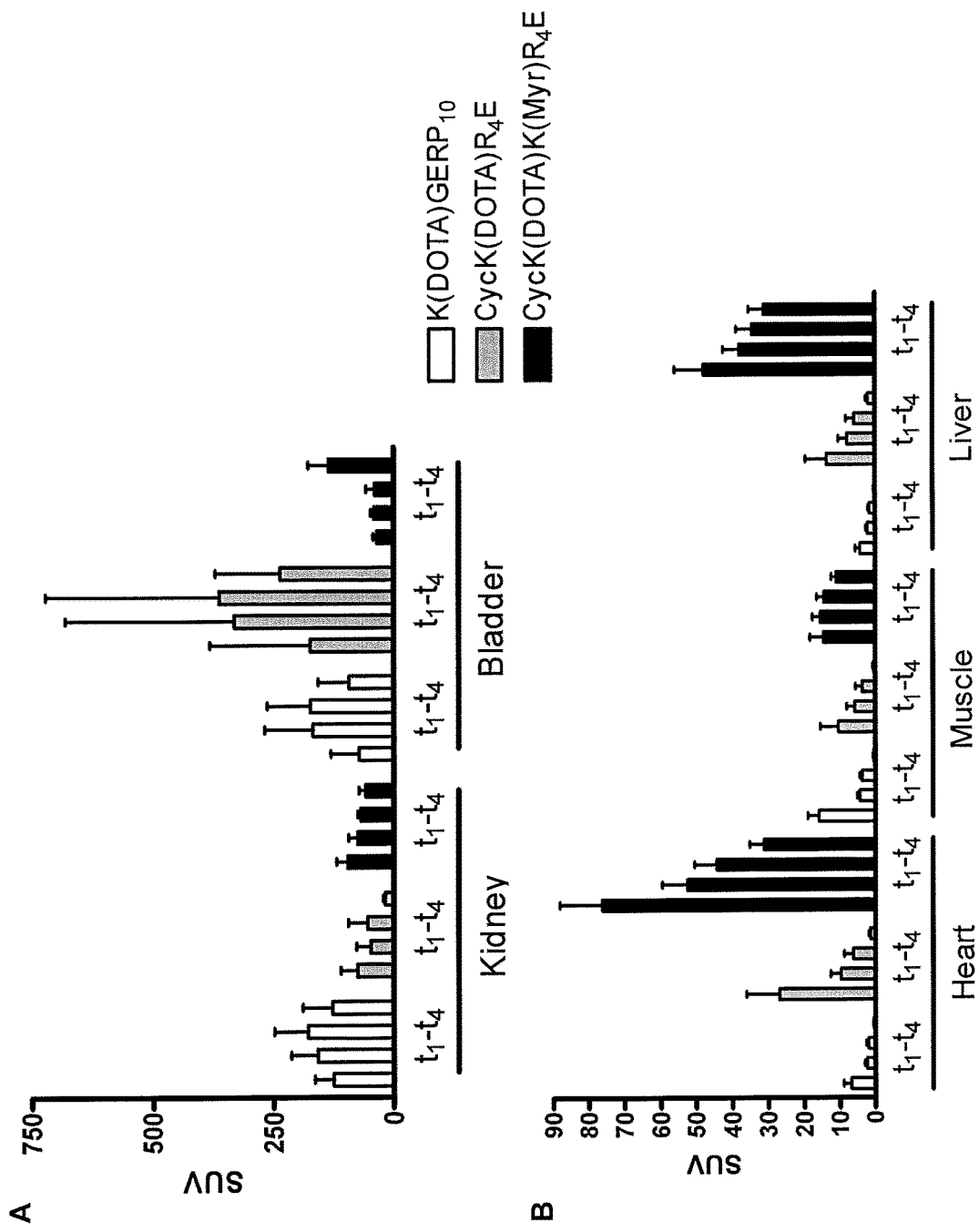
FIG. 6. Comparison of distribution of scavenger peptides over time.
Shown are standardized uptake values (SUV) determined by PET in mice injected with the $^{68}$Ga labeled peptides K(DOTA)GERP$_{10}$, CycK(DOTA)R$_4$E, CycK(DOTA)K(Myr)R$_4$E. SUV values of the peptides for time points $t_1$=0-20 min, $t_2$=20-40 min, $t_3$=40-60 min and 4=120-140 min are shown for kidney and bladder (A) as well as heart, muscle and liver (B). Values in the bladder are lower for the myristic acid coupled peptide CycK(DOTA)K(Myr)R$_4$E in comparison to K(DOTA)GERP$_{10}$ and CycK(DOTA)R$_4$E while levels are similar in the kidney. SUV values in the heart, muscle and liver are higher for CycK(DOTA)K(Myr)R$_4$E compared to the fatty acid free peptides. This confirms that the peptide CycK(DOTA)K(Myr)R$_4$E circulates for over 140 min ($t_4$) while both K(DOTA)GERP$_{10}$ and CycK(DOTA)R$_4$E are completely excreted after 140 min.
Figure 7:
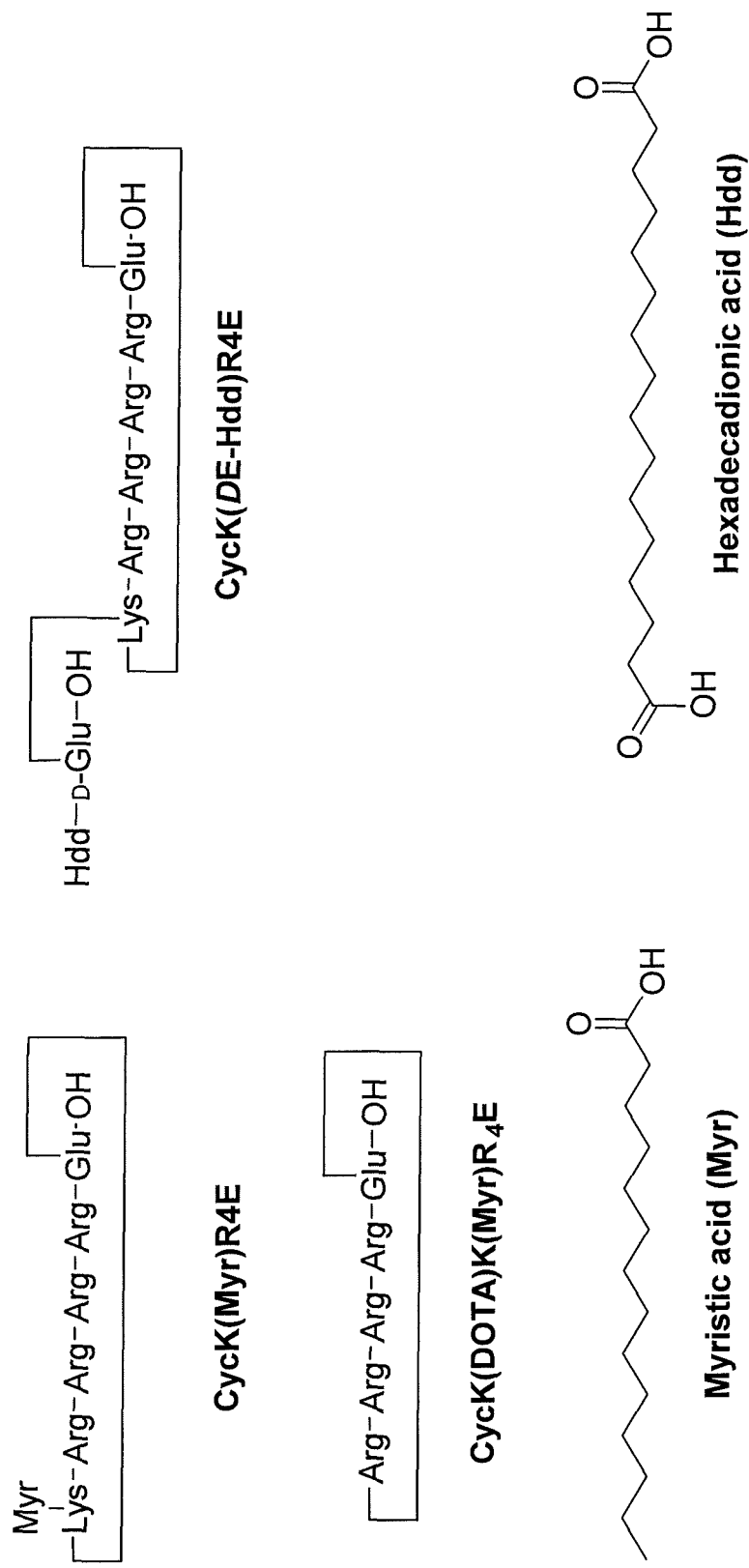
FIG. 7. Comparison of structure of Hdd vs Myr coupled scavenger peptide.
Figure 8:
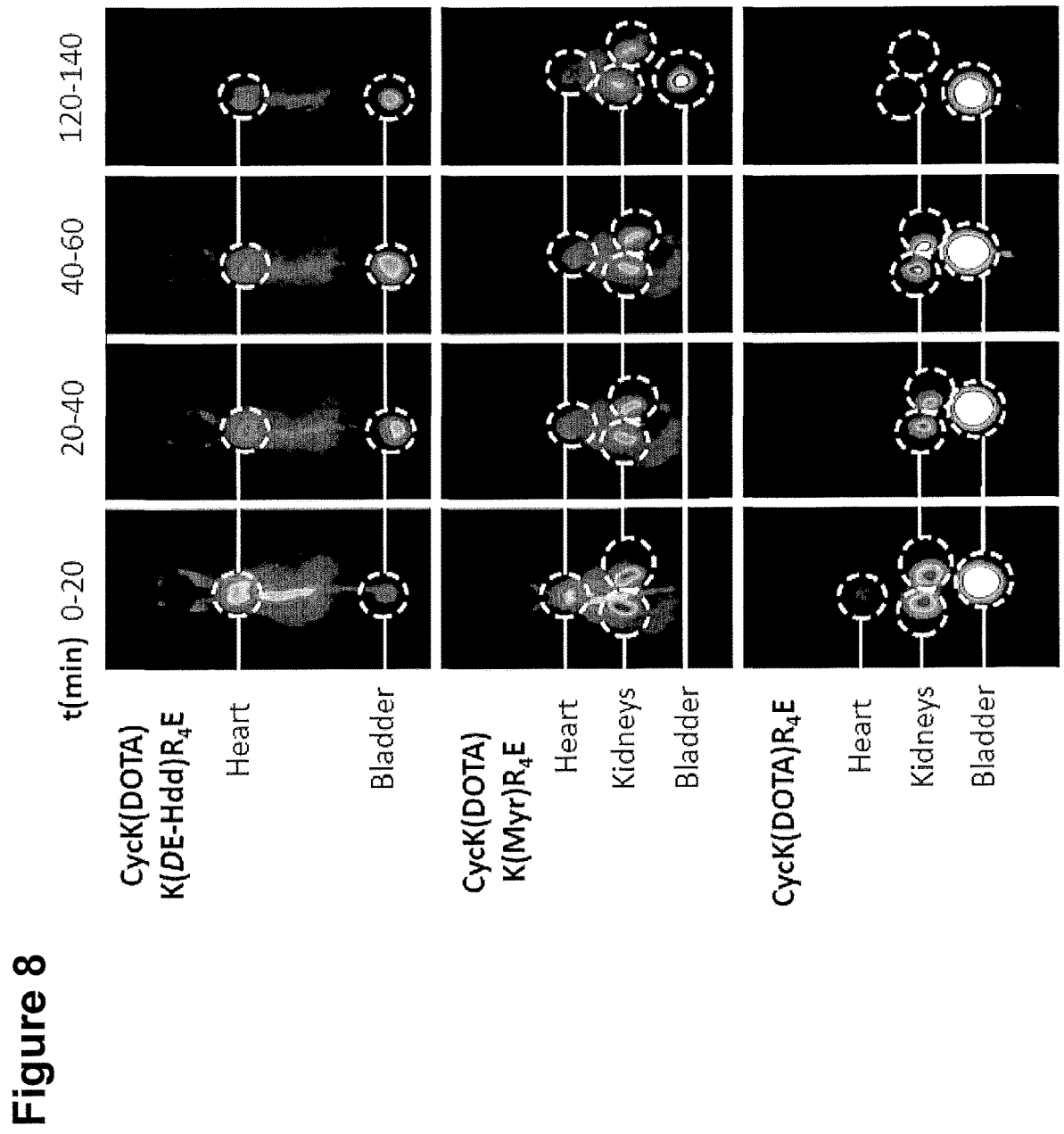
FIG. 8. PET analysis of fatty acid modified peptides.
PET analysis of fatty acid modified peptides CycK(DOTA)K(DE-Hdd)R$_4$E and CycK(DOTA)K(Myr)R$_4$E as well as the fatty acid free peptide CycK(DOTA)R$_4$E. Both fatty acid modified peptides (top and medium row) remain in the animals for over 2 h whereas the fatty acid free peptide is excreted almost completely after 20 min (bottom row; only kidney and bladder show signal starting from 20-40 min). One difference between the Hdd and the Myr coupled peptides is that the former appears in the bladder without accumulation in the kidneys whereas the latter shows a strong accumulation in the kidneys prior to excretion through the bladder. Such an accumulation in the kidneys could lead to side effects so that the Hdd coupled peptide is favourable in that respect.
Figure 9:
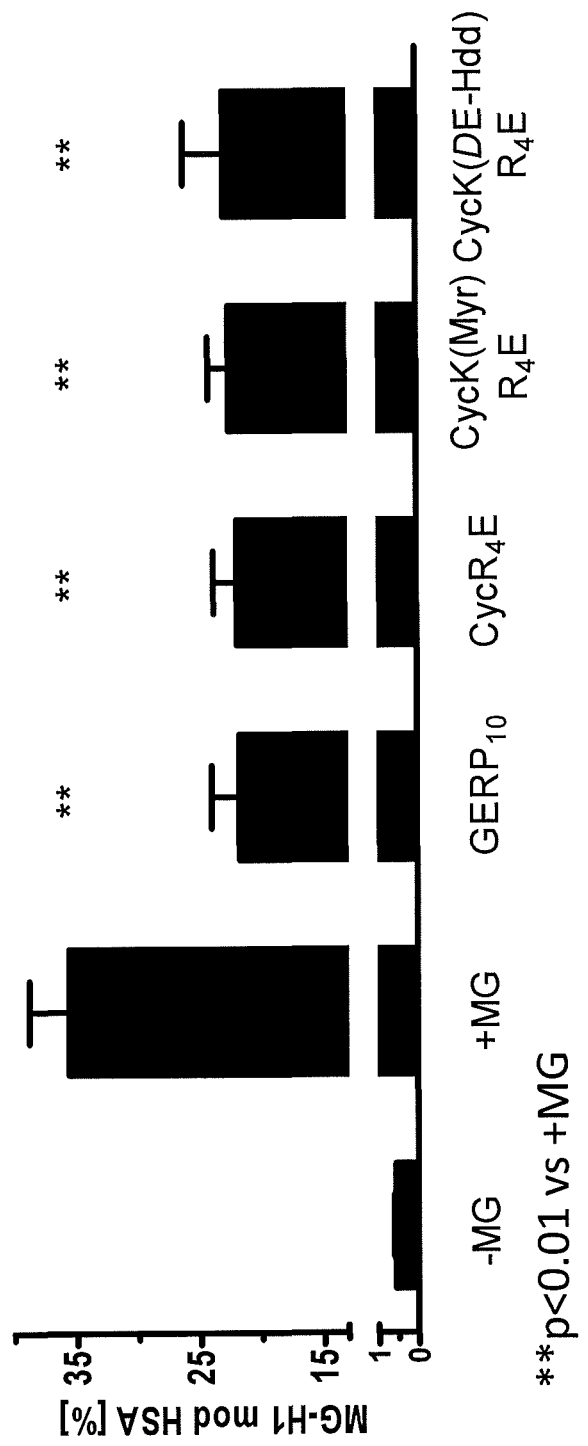
FIG. 9. Protective effect of scavenger peptides on MG-H1 modification of HSA. Peptides (400 μM) were co-incubated with HSA (400 μM) and methylglyoxal (MG; 200 μM) and the amount of MG-H1 modified HSA was quantified. Cyclic peptides were tested without fatty acid modification (CycR$_4$E), with myristic acid modification (CycK(Myr)R$_4$E) as well as with a hexadecanedioic acid modification via a D-glutamic acid linker (CycK(DE-Hdd)R$_4$E. All four peptides significantly prevented modification of HSA with MG-H1.
Figure 10:
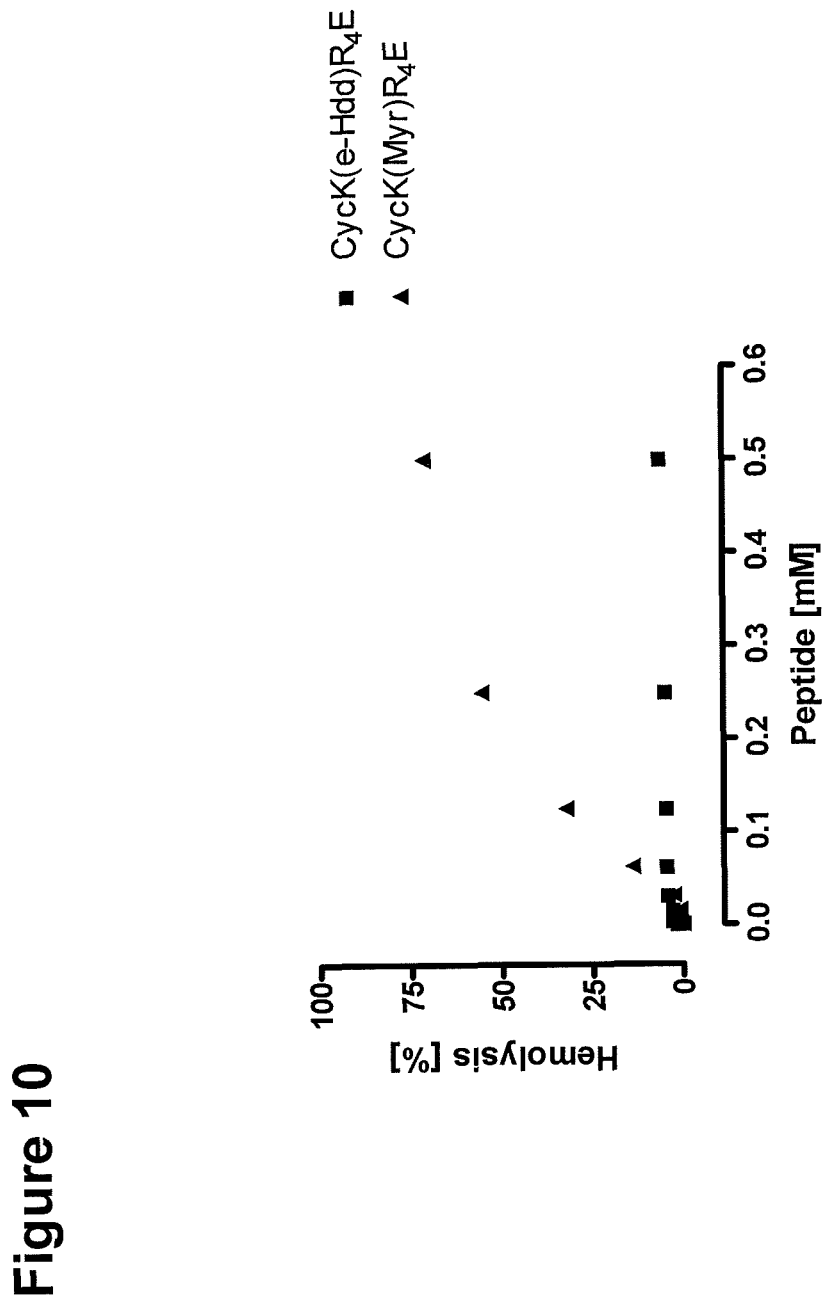
FIG. 10. Hemolytic effect of the scavenger peptides.
Shown is the hemolytic effect of CycK(e-Hdd)R$_4$E (square) and CycK(Myr)R$_4$E (triangle). Washed human whole blood was incubated with peptides at indicated concentrations. The absorbance of the supernatant was quantified after centrifugation and compared to blood incubated with surfactant (100% hemolysis) as positive- and saline (0% hemolysis) as negative control. CycK(Myr)R$_4$E displays significant hemolysis at concentrations over 50 μM while CycK(e-Hdd)R$_4$E does not cause hemolysis even at high concentrations.
Figure 11:
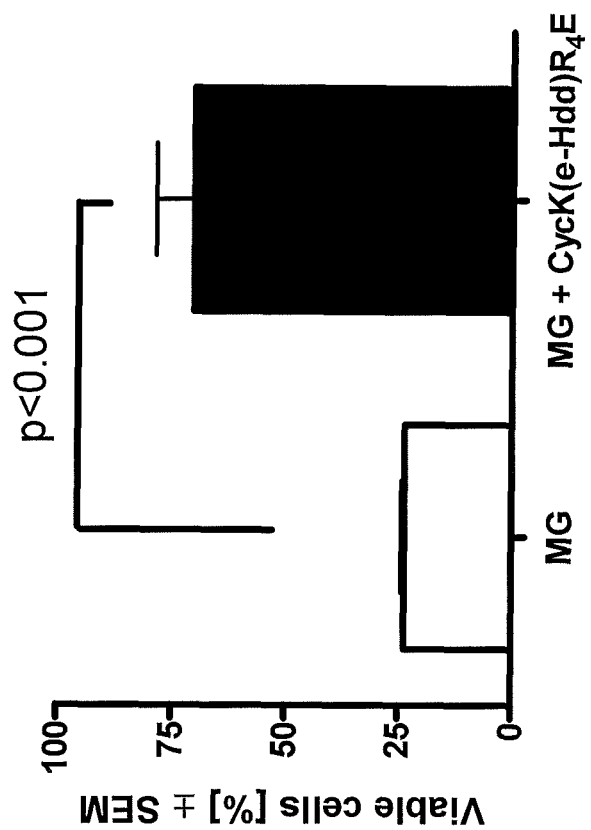
FIG. 11. Prevention of MG induced toxicity.
Figure 12:
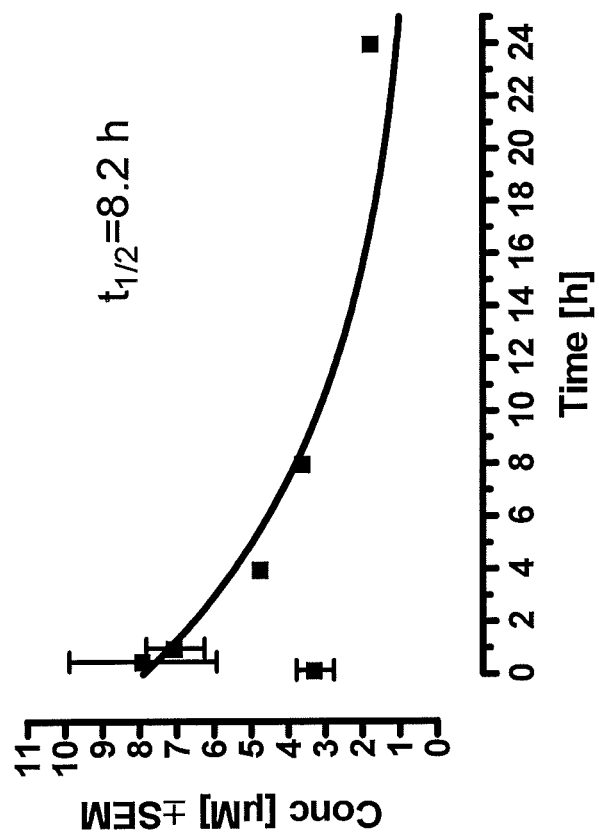

FIG. 12. Pharmacokinetic of the peptide CycK(e-Hdd)R$_4$E.

Pharmacokinetic of CycK(e-Hdd)R$_4$E was determined in C57/B16 mice. Peptide was injected i.p. (0.25 mg/mouse) and plasma was collected at indicated time points. Concentration of the peptide was quantified by LC MS measurement. Half-life was determined to be approximately 8 h using a one phase exponential decay fit.

EXAMPLES

1. Methods 1.1 Peptide Synthesis

Peptides were synthesized on solid phase, using Fmoc-chemistry. Coupling of amino acids (10 eq.) was carried out with HBTU (9.8 eq.) and DIPEA (20 eq.) in NMP and Fmoc was removed by incubation in 20% piperidine/NMP unless noted otherwise. After coupling and deprotection, resin was washed with NMP. For synthesis of CycR$_4$E, CycK(Myr)R$_4$E and CycK(DOTA)R$_4$E, CTC-resin (1.1 mmol/g, 200 mg) was loaded with 50 μmol Fmoc-Glu(OAll)-OH in the presence of DIPEA (2 eq.) in DCM for 1 h. Remaining active sites were capped by incubation with DCM/MeOH/DIPEA at a ratio of 17/2/1 for 30 min. Four Fmoc-Arg(Pbf)-OH were coupled and Fmoc of the fourth Fmoc-Arg(Pbf) was removed. For CycR$_4$E OAll was removed by incubation with Tetrakis(triphenylphosphine)palladium(0) (20 mg/100 μmol peptide) and dimethylaminoboran (100 mg/100 μmol peptide) in DCM for 20 min, next. Resin was washed with 10% ethanolamine/DCM for 5 min twice followed by washes with DCM, MeOH, DCM and NMP. CycR4E was cyclized with PyAOP (5 eq.) and DIPEA (7.5 eq.) in NMP for 1 h at RT. For CycK(Myr)R$_4$E and CycK(DOTA)R$_4$E, Alloc-Lys(Fmoc)-OH was coupled instead of palladium catalyzed removal of OAll. Next Myristic acid (10 eq. with 9.8 eq. HBTU and 20 eq. DIPEA in NMP) for CycK(Myr)R$_4$E or DOTA-tris(tBu)ester (2 eq. with 1.8 eq. COMU and 4 eq. DIPEA in NMP overnight) for CycK(DOTA)R$_4$E was attached to the side chain of Lys after removal of Fmoc. CycK(myr)R$_4$E and CycK(DOTA)R$_4$E were cyclized with diphenylphosphonic azide (7.5 eq.) and DIPEA (5 eq.) in NMP overnight after palladium catalyzed removal of Alloc and OAll as was described for CycR$_4$E.

The peptide standards CycK(Myr)R$_3$MG-H1E, CycK(Myr)R$_2$MG-H1E, CycK(Myr)RMG-H1R$_2$E and CycK(Myr)MG-H1R$_3$E were synthesized equivalent to CycK(Myr)R$_4$E while one of the four arginines was replaced with MG-H1 in each of the four arginine positions. MG-H1 was introduced as a Fmoc and bis(4-methoxyphenyl)methyl (Dod) protected amino acid (Fmoc-MG-H1(Dod)-OH) which was synthesized as described previously (Wang et al., 2012). Coupling of Fmoc-MG-H1(Dod)-OH (2 eq.) was carried out in NMP with DIPEA (4 eq.) and COMU (1.8 eq.) for 2 h at RT and the coupling procedure was repeated once without cleaving off Fmoc.

CycK(DE-Hdd)R$_4$E (i.e. CycK(e-Hdd)R$_4$E) was synthesized on Wang resin with a loading of 0.22 mmol/g. Fmoc-Glu(OAll)-OH (4 eq.) was loaded onto the resin (200 mg 44 μmol, 1 eq.) via Mitsunobo reaction employing triphenylphosphine (4 eq.) and diisopropylazodicarboxylate (4 eq.) in THF. The reaction was left to proceed for 2 h at RT on a shaker. Fmoc was removed by incubation in 20% piperidine/NMP for 2×10 min. Arginine was coupled via Fmoc-Arg(Pbf)-OH (10 eq.) with HBTU (9.8 eq.) and DIPEA (20 eq.) in NMP for 30 min at RT and Fmoc was removed by incubation in 20% piperidine/NMP unless noted otherwise. This procedure was repeated 3 times. Fmoc-Lys(Mtt)-OH (2 eq.) was coupled with COMU (1.8 eq.) and DIPEA (4 eq.) in NMP overnight. Fmoc was removed and OAll was removed by incubation with Tetrakis(triphenylphosphine)palladium(0) (20 mg/100 μmol peptide) and dimethylaminoboran (100 mg/100 μmol peptide) in DCM for 20 min. Resin was washed with 10% ethanolamine/DCM for 5 min twice followed by washes with DCM, MeOH, DCM and NMP. N-terminal to glutamic acid side chain cyclisation was carried out with 5 eq. PyAOP (521 g/mol) and 7.5 eq. of DIPEA (Triethylamin for cyclisation in solution) in NMP for 1 h. Side chain protection group Mtt was removed by incubation with 3.5% TCA/DCM twice (yellow colour of resin and solution) followed by incubation with 3.5% TCA/2.5% TIS/DCM for 2 h. Fmoc-D-Glu(OtBu) (2 eq.) was coupled with COMU (1.8 eq.) and DIPEA (4 eq.). Fmoc was removed and hexadecanedioic acid (1.2 eq.) was coupled with COMU (1 eq.).

20 pentapeptides AXRAA were synthesized, where X was replaced with each of the canonical amino acids. Synthesis was carried out on CTC resin (1.1 mmol/g, 100 mg resin) which was loaded with 25 μmol of Fmoc-Ala-OH in the presence of DIPEA (2 eg.) in DCM for 1 h. Subsequent amino acids were coupled and the N-terminus was acetylated by incubation with acetic anhydride (10 eq.) and DIPEA (20 eq.) for 30 min in NMP.

The peptides CycK(DOTA)K(Myr)R$_4$E, K(DOTA)K(Myr)R$_4$E and CycK(DOTA)K(Myr)MG-H1$_4$E were synthesized on Wang-Resin. MG-H1 was introduced as Fmoc-MG-H1(Dod)-OH). Resin (25 μmol) was loaded with Fmoc-Glu(OAll)-OH (2 eq) in the presence of triphenylphosphine (3 eq) and diisopropyl azodicarboxylate (3 eq) in THF at RT for 2 h. Four Fmoc-Arg(Pbf)-OH or four Fmoc-MG-H1(Dod)-OH followed by Fmoc-Lys(Mtt)-OH and Alloc-Lys(Fmoc)-OH were coupled. DOTA-tris(tBu)ester and myristic acid were coupled to the side chain of Alloc-Lys(Fmoc)-OH and Fmoc-Lys(Mtt)-OH, respectively. The peptides CycK(DOTA)K(Myr)R$_4$E and CycK(DOTA)K(Myr)MG-H1$_4$E but not K(DOTA)K(Myr)R$_4$E were cyclized using diphenylphosphonic acid (7.5 eq) and DIPEA (5 eq) in NMP overnight after palladium catalyzed removal of Alloc and OAll as described above.

The peptides GERP$_{10}$ (SEQ ID NO. 18) and K(DOTA)GERP$_{10}$ (SEQ ID NO. 19) (50 μmol) were synthesized on a Rink amide resin on an ABI 433 A peptide synthesizer with 10 eq of Fmoc-Gly-OH, Fmoc-Glu(tBu)-OH, Fmoc-Arg(Pbf)-OH, Fmoc-Pro-OH. After synthesis of GERP$_{10}$ (SEQ ID NO. 18), the resin was split into two parts. One part was cleaved off of the resin and Fmoc-Lys(Alloc)-OH was added to the other part. DOTA-tris(tBu)ester was coupled after palladium catalyzed removal of Alloc as was described above.

Free peptides were obtained by incubation in TFA containing 2.5% TIS and 2.5% $H_2O$ for 2 h at RT. Exceptions were peptides containing DOTA-tris(tBu) and MG-H1 (Dod)-OH which were obtained by incubation in 5% ethandithiole in TFA for up to 24 h. Peptides were precipitated and washed in cold diethyl ether and purified by reverse phase HPLC. LC MS analysis of peptides was carried out with an Exactive Orbitrap instrument (Thermo Scientific, USA) with the following results, shown in Table 3.

TABLE 3

| Peptide [SEQ ID NO.] | exact mass theoretical | experimental |
| --- | --- | --- |
| CycK(Myr)$R_4$E | $[m + 2H]^{2+}$ = 546.8774 | $[m + 2H]^{2+}$ = 546.8983 |
| CycR$_4$E | $[m + H]^{+}$ = 745.4543 | $[m + H]^{+}$ = 745.5060 |
| GERP$_{10}$ [18] | $[m + 4H]^{4+}$ = 1103.5547 | $[m + 4H]^{4+}$ = 1103.5551 |
| CycK(DOTA)K(Myr)$R_4$E | $[m + 2H]^{2+}$ = 804.0150 | $[m + 2H]^{2+}$ = 804.0287 |
| CycK(DOTA)$R_4$E | $[m + H]^{+}$ = 1268.7294 | $[m + H]^{+}$ = 1268.8356 |
| K(DOTA)GERP$_{10}$ [19] | $[m + 4H]^{+}$ = 1232.1235 | $[m + 4H]^{+}$ = 1232.1245 |
| K(DOTA)K(Myr)$R_4$E [20] | $[m + 2H]^{2+}$ = 813.0203 | $[m + 2H]^{2+}$ = 813.0269 |
| CycK(Myr)$R_3$MG-H1 | $[m + H]^{+}$ = 1146.5820 | $[m + H]^{+}$ = 1146.6365 |
| CycK(Myr)$R_2$MG-H1RE | $[m + H]^{+}$ = 1146.5820 | $[m + H]^{+}$ = 1146.7676 |
| CycK(Myr)RMG-H1$R_2$E | $[m + H]^{+}$ = 1146.5820 | $[m + H]^{+}$ = 1146.7585 |
| CycK(Myr)MG-H1$R_3$E | $[m + H]^{+}$ = 1146.5820 | $[m + H]^{+}$ = 1146.7596 |
| CycK(DOTA)K(Myr)MG-H1$_4$E | $[m + H]^{+}$ = 1823.0650 | $[m + H]^{+}$ = 1823.1533 |
| AARAA [9] | $[m + H]^{+}$ = 501.2780 | $[m + H]^{+}$ = 501.3151 |
| ACRAA [4] | $[m + H]^{+}$ = 533.2500 | $[m + H]^{+}$ = 533.2499 |
| ADRAA [16] | $[m + H]^{+}$ = 545.2678 | $[m + H]^{+}$ = 545.3080 |
| AERAA [17] | $[m + H]^{+}$ = 559.2834 | $[m + H]^{+}$ = 559.2836 |
| AFRAA [11] | $[m + H]^{+}$ = 577.3093 | $[m + H]^{+}$ = 577.3120 |
| AHRAA [14] | $[m + H]^{+}$ = 567.2998 | $[m + H]^{+}$ = 567.3421 |
| AKRAA [3] | $[m + H]^{+}$ = 558.3358 | $[m + H]^{+}$ = 558.3773 |
| ALRAA [13] | $[m + H]^{+}$ = 543.3249 | $[m + H]^{+}$ = 543.3643 |
| AMRAA [12] | $[m + H]^{+}$ = 561.2813 | $[m + H]^{+}$ = 561.2812 |
| ANRAA [10] | $[m + H]^{+}$ = 544.2838 | $[m + H]^{+}$ = 544.2845 |
| AQRAA [6] | $[m + H]^{+}$ = 558.2994 | $[m + H]^{+}$ = 558.2990 |
| ARRAA [2] | $[m + H]^{+}$ = 586.3420 | $[m + H]^{+}$ = 586.3419 |
| ASRAA [15] | $[m + H]^{+}$ = 517.2729 | $[m + H]^{+}$ = 517.2736 |
| AVRAA [5] | $[m + H]^{+}$ = 529.3093 | $[m + H]^{+}$ = 529.3096 |
| AWRAA [8] | $[m + H]^{+}$ = 616.3202 | $[m + H]^{+}$ = 616.3198 |
| AYRAA [7] | $[m + H]^{+}$ = 593.3042 | $[m + H]^{+}$ = 593.3045 |

1.2 Positron Emission Tomography (PET) Analysis

DOTA coupled peptides were labeled with $^{68}$Ga as described previously (Wischnjow et al., 2016). In short $^{68}$Ga was eluted from the generator into a tube containing 20 nmol of the peptide and 0.5% ascorbic acid in 0.5 M Na-acetate buffer. The mixture was incubated at pH 3.5-4.0 for 10' at 95° C. while stirring to allow for the $^{68}$Ga-DOTA complex to form. Free $^{68}$Ga was removed using C18 solid phase extraction cartridges (Thermo Scientific, USA) and the product was checked by HPLC (Agilent Technologies, USA) equipped with a radio flow detector. The labeled peptide was injected i.v. into NMRI mice. PET analysis was carried out for 0-1 h and for another 20' after 2 h while cumulative pictures are shown for 0-20 min, 40-60 min and 120-140 min.

Data was normalized for animal weight and injected dose and pictures and data are given as standardized uptake value [SUV]. For quantitative comparison the area under the curve for the SUV values of the different regions was determined and compared by Student's t-test.

1.3 Serum Stability

The cyclic peptide CycK(DOTA)K(Myr)$R_4$E and the linear peptide K(DOTA)K(Myr)$R_4$E were labeled with $^{177}$Lu. In short 20 nmol of peptides were incubated with $^{177}$Lu in 0.4 M Na-acetate buffer (pH 5.0) for 10' at 95° C. Free $^{177}$Lu was removed by C18 solid phase extraction cartridges, the products eluted with EtOH and checked by radio-HPLC. The radiolabelled peptides were reconstituted in human serum (H4522; Sigma-Aldrich) and incubated in serum at 37° C. for the times indicated. Serum was precipitated by addition of two parts acetonitrile centrifuged for 10 min at 13000 g and the supernatant analysed by HPLC (Agilent Technologies, USA) fitted with a radio flow detector using a 10 min gradient of 0-60% acetonitrile in water (0.1% TFA).

1.4 Competitive Inhibition of HSA MG-H1 Formation

MG was synthesized as described previously (Rabbani et al., 2014). In short, pure MG-1,1-dimethylacetal was heated in sulphuric acid solution for 1 h and fractionally distilled in a column containing glass helices under reduced pressure. Fractions were analyzed by $^1$H and $^{13}$C NMR. The last fraction contained pure MG. Scavengers (400 μM) were incubated with HSA (400 μM) and MG (200 μM) in 0.1 M phosphate buffer pH 7.4 at 37° C. for 48 h. Two parts urea (8M urea, 0.5 M TrisHCl; pH8.0) were added to the solution and the sample was vortexed. HSA was precipitated by addition of two parts acetonitrile (respective to the final sample/urea mixture) and collected by centrifugation for 10' at 13000 g. Peptide scavengers were not precipitated but remained in the supernatant using this procedure. The HSA containing pellet was dissolved in 20 mM HCl and the protein content was determined by BCA assay. Equal amounts of HSA were hydrolysed by serial enzymatic digestion using pepsin, pronase E, aminopeptidase and prolidase as described previously (Thornalley et al., 2003). The amount of HSA-MG-H1 adduct was determined by LC-MS. Samples and standard curve were spiked with d3-MG-H1 (Polypeptide Group, San Diego, Calif., USA) and derivatized with Fmoc-Cl. Separation was performed on a C18 column (Hypersil Gold aQ; Thermo Scientific, USA) using a 20 min gradient of 0-100% acetonitrile (0.1% TFA) with the first five minutes diverted to waste. Analysis was carried out on an Exactive Orbitrap MS system (Thermo Scientific, USA). The Fmoc-MG-H1 (m+H: 451.20; m+H$_{theor}$: 451.20) and the Fmoc-d3-MG-H1 (m+H: 454.21; m+H$_{theor}$: 454.22) adduct eluted after 13.88 min. The calibration range used for the assay was 0-30 pmol.

1.5 Pain Response by Hot Plate Assay and MG-Scavenging in Mice

C57BL/6 mice (Charles River, Boston, USA) were acclimatized for 1 week prior to testing. A total of 36 mice were randomly assigned to three groups. One group received the peptide CycK(Myr)R$_4$E (0.25 mg/mouse in 0.9% NaCl) ip while the two other groups received saline IP. One of the saline and the peptide treated group received MG (5 µg/g) iv 30 min after peptide/saline injection while the third group received saline iv. Pain response was tested using a hot plate analgesia meter (Columbus Instruments, Ohio, USA) with the plate set to 50° C. 3 h after MG injection. Mice were removed from the plate when hind parc lifting, licking, shaking or jumping occurred. Mice were removed after a maximal cut-off time of 60 s. Pain response for each animal was measured in triplicates.

To determine the effect of the peptide on the MG-plasma levels, mice received the same treatment as described for the pain response assay. Then blood was collected through the submandibular vein into EDTA tubes 30 min after MG injection. Samples were spun for 5 min at 3,000 g at 4° C., the supernatant frozen in liquid N$_2$ and stored at −80° C. until analysis. MG content was determined by LC-MS/MS analysis as described below.

1.6 MG Scavenging In Vitro

Scavengers (400 µM) were incubated with MG (200 µM) in 0.1 M phosphate buffer, pH 7.4 at 37° C. The kinetics of the scavenging reaction was followed for 48 h. Samples were frozen in liquid nitrogen and stored at −80° C. until analysis. MG content was quantified by HPLC as described below.

1.7 MG Quantification by HPLC and LC MS/MS

MG was quantified using previously published methods based on HPLC for the in vitro assay or LC-MS/MS for the in vivo analysis.[3] In short samples were precipitated with 20% TCA at a ratio of 2/1 and vortex mixed. Internal standards $^{13}$C MG (LC-MS/MS analysis) or 2,3-dimethylquinoxaline (HPLC analysis) and water was added and the sample mixed again. Samples were centrifuged at 13,000 g at 4° C. for 5 min and the supernatant derivatized with 1,2-diaminobenzene in the presence of sodium azide for 4 h at RT. For HPLC based MG analysis the linear gradient was 0-6% acetonitrile in 15 min. The MG-1,2-diaminobenzene adduct 2-methylquinoxaline and the internal standard 2,3-dimethylquinoxaline were detected with a UV monitor at 320 nm and eluted at 12.7 min and 14.2 min, respectively. For LC-MS/MS, samples were analyzed using an ACQUITY UPLC I equipped with a Xevo TQ-S mass spectrometer (Waters, USA). Samples were separated on BEH C$_{18}$ analytical column (2.1×50 mm, 1.7 µm) fitted with pre-column (2.1×5 mm, 1.7 µm). Solvent A was water+0.1% formic and solvent B was 50% acetonitrile+0.1% formic acid and a linear gradient from 0-100% solvent B, over ten minutes was used with a flow rate of 0.2 ml/min. Injection volume was 1 µl and the column temperature was 20° C. The quinoxaline analytes were detected by electrospray positive ionization-mass spectrometric multiple-reaction monitoring (MRM). The source temperature was 150° C. and the desolvation gas temperature was 350° C. The cone gas and desolvation gas flow rates were 150 and 800 l/hr, respectively. The capillary voltage was 0.5 kV and the cone voltage was 20V. Mass transitions (parent ion >fragment ion; collision energy) and retention time were as follows: MG 145.01>77.10; 24 eV, 5.93 mins; [$^{13}$C$_3$]-MG 148.07>77.16; 24 eV, 5.92 mins. The standard curve was in the range of 0-20 pmol and 0-1 nmol for LC MS/MS analysis and HPLC analysis, respectively.

1.8 Detection of MG-Modified Scavenger Peptides by LC-MS/MS

For LC-MS/MS analysis plasma obtained from mice or a type 2 diabetes patient was precipitated with 2 parts acetonitrile, vortexed and centrifuged for 10 min at 13000 g. The supernatant was analyzed by LC-MS/MS (Xevo TQ S, Waters, USA) on a BEH C$_{18}$ analytical column (2.1×100 mm, 1.7 µm) fitted with pre-column (2.1×5 mm, 1.7 µm) (Xevo TQ S, Waters, USA). Solvent A was water with 0.1% formic acid and solvent B was acetonitrile+0.1% formic acid. A linear gradient from 0-40% solvent B at a flow rate of 0.4 ml/min and a column temperature of 40° C. was used. Peptides CycK(Myr)R$_4$E and the MG-H1 modified versions CycK(Myr)R$_3$MG-H1E, CycK(Myr)R$_2$MG-H1RE, CycK(Myr)RMG-H1R$_2$E and CycK(Myr)MG-H1R$_3$E eluted after 12.15 min, 12.40 min, 12.50 min, 12.52 min and 12.90 min, respectively. Mass transitions, collision energy and retention time (parent ion >fragment ion; collision energy, retention time) were as follows:

CycK(Myr)R$_4$E 365.032>412.373; 18.0 eV and 365.032>335.974; 18.0 eV, 12.15 mins CycK(Myr)R$_3$MG-H1E 382.904>460.400; 16 eV and 287.543>312.959; 10 eV, 12.40 mins CycK(Myr)R$_2$MG-H1RE 382.904>460.400; 16 eV and 287.543>312.959; 10 eV, 12.50 mins CycK(Myr)RMG-H1R$_2$E 382.904>460.400; 16 eV and 287.543>312.959; 10 eV, 12.52 mins CycK(Myr)MG-H1R$_3$E 382.904>460.400; 16 eV and 287.543>312.959; 10 eV, 12.90 mins

1.9 Statistical Analysis

Data was analyzed by one-way ANOVA and Tukey-Kramer post-hoc test. PET data was analyzed by comparison of the area under the curve of the SUV values by Student's t-test.

1.10 Hemolysis of CycK(e-Hdd)R$_4$E and CycK(Myr)R$_4$E

Human whole blood was collected into EDTA tubes and centrifuged at 500 g at RT for 5 min. The plasma and buffy coat was removed and saline solution was added to the haematocrit containing pellet to the previous plasma level to wash the erythrocytes. The tube was gently inverted several times and centrifuged again at 500 g. This procedure was repeated until the supernatant remained clear (approx. 4 times). After the last centrifugation step the hematocrit was re-suspended in PBS to reach the original blood volume. Increasing amounts of peptide in saline solution were mixed with washed blood at a ratio of 1/1 and incubated at 37° C. for 30 min. Samples were centrifuged at 13000 g for 5 min and absorbance (554 nm) of the supernatant was determined.

Haemolysis was compared to saline solution (negative control; 0% haemolysis) and 1% Triton X100 solution (positive control; 100% haemolysis).

1.11 Prevention of MG Induced Toxicity

Murine cardiac endothelial cells were seeded on gelatine pre-coated 96 well plates at a density of 5000 cells per well in DMEM (1 g/l glucose, 5% FCS, 1% Pen/Strep, 1% AmpB, 1% HEPES). On the following day cells were switched to medium containing only 0.1% FCS. Cells were subsequently stimulated with methylglyoxal or methylglyoxal pre-incubated with CycK(e-Hdd)$R_4$E and incubated for 48 h. MTT ((3-(4,5-Dimethylthiazol-2-yl)-2,5-Diphenyltetrazolium Bromide)) solution (50 µl of 2 mg/ml in PBS) was added to the wells and the plate was incubated at 37° C. for 3-4 h. Medium was removed and 200 µl of DMSO was added to lyse cells and solubilise the purple formazan crystals. The plate was incubated for 1 h at room temperature on a shaker and absorbance was measured at 590 nm. Intensity for untreated cells was set to 100%.

1.12 PK of CycK(e-Hdd)$R_4$E in Mice

Ten week old C57/Bl6 mice were injected with CycK(e-Hdd)$R_4$E (0.25 mg/mouse i.p. in 200 µl saline solution). Blood was collected by cardiac puncture in an aesthetised mice at time points 10', 30', 1 h, 4 h, 8 h and 24 h into tubes containing EDTA. Plasma was collected after centrifugation at 3000 g for 5' at room temperature and frozen in liquid nitrogen.

The peptide CycK(Myr)$R_4$E was spiked as an internal standard. Plasma was acidified with 5% TFA (5 µl/30 µl), acetonitrile (60 µl) was added and the tubes vortexed. Another 120 µl of acetonitrile were added and samples were ultrasonicated for 5 min. Samples were spun for 20 min at 13000 g. The supernatant (180 µl) was collected, mixed with 180 µl of water and freeze dried. The sample was resuspended in 30 µl of a mixture of acetonitrile/water (ratio of 1/1) containing 0.1% TFA. The samples was analysed by LC MS. Concentration was calculated by normalisation for the internal standard in combination with linear regression of a standard curve. Concentration/time-points were fitted using a one phase exponential decay model to determine the half-life of the drug.

The features disclosed in the foregoing description, in the claims and/or in the accompanying drawings may, both separately and in any combination thereof, be material for realizing the invention in diverse forms thereof.

REFERENCES

F. M. Abu-Zidan, L. D. Plank and J. A. Windsor, *Eur J Surg* 2002, 168, 119-123.
S. Agalou, N. Ahmed, A. Dawnay and P. J. Thornalley, *Biochem Soc Trans* 2003, 31, 1394-1396.
N. Ahmed, U. Ahmed, P. J. Thornalley, K. Hager, G. Fleischer and G. Munch, *J Neurochem* 2005, 92, 255-263.
M. Aksenov, M. Aksenova, D. A. Butterfield and W. R. Markesbery, *J Neurochem* 2000, 74, 2520-2527.
M. Y. Aksenov, M. V. Aksenova, D. A. Butterfield, J. W. Geddes and W. R. Markesbery, *Neuroscience* 2001, 103, 373-383.
J. Anguizola, R. Matsuda, O. S. Barnaby, K. S. Hoy, C. Wa, E. DeBolt, M. Koke, D. S. Hage, *Clinica chimica acta; international journal of clinical chemistry* 2013, 425, 64-76.
P. J. Beisswenger, S. K. Howell, A. D. Touchette, S. Lal, B. S. Szwergold, *Diabetes* 1999, 48, 198-202.
P. J. Beisswenger, K. S. Drummond, R. G. Nelson, S. K. Howell, B. S. Szwergold, M. Mauer, *Diabetes* 2005, 54, 3274-3281.
P. J. Beisswenger, S. K. Howell, G. B. Russell, M. E. Miller, S. S. Rich, M. Mauer, *Diabetes Care* 2013, 36, 3234-3239.
A. Bierhaus, T. Fleming, S. Stoyanov, A. Leffler, A. Babes, C. Neacsu, S. K. Sauer, M. Eberhardt, M. Schnolzer, F. Lasitschka, W. L. Neuhuber, T. I. Kichko, I. Konrade, R. Elvert, W. Mier, V. Pirags, I. K. Lukic, M. Morcos, T. Dehmer, N. Rabbani, P. J. Thornalley, D. Edelstein, C. Nau, J. Forbes, P. M. Humpert, M. Schwaninger, D. Ziegler, D. M. Stern, M. E. Cooper, U. Haberkorn, M. Brownlee, P. W. Reeh, P. P. Nawroth, *Nature medicine* 2012, 18, 926-933.
F. Boscia, I. Grattagliano, G. Vendemiale, T. Micelli-Ferrari and E. Altomare, *Invest Ophthalmol Vis Sci* 2000, 41, 2461-2465.
S. Brings, S. Zhang, Y. S. Choong, S. Hogl, M. Middleditch, M. Kamalov, M. A. Brimble, D. Gong, G. J. Cooper, *Biochimica et biophysica acta* 2015, 1852, 1610-1618.
D. A. Butterfield and C. M. Lauderback, *Free Radic Biol Med* 2002, 32, 1050-1060.
A. Castegna, M. Aksenov, V. Thongboonkerd, J. B. Klein, W. M. Pierce, R. Booze, W. R. Markesbery and D. A. Butterfield, *J Neurochem* 2002, 82, 1524-1532.
K. Chen, M. Kazachkov and P. H. Yu, *J Neural Transco (Vienna)* 2007, 114, 835-839.
J. Choi, C. A. Malakowsky, J. M. Talent, C. C. Conrad and R. W. Gracy, *Biochem Biophys Res Commun* 2002, 293, 1566-1570.
C. C. Conrad, P. L. Marshall, J. M. Talent, C. A. Malakowsky, J. Choi and R. W. Gracy, *Biochem Biophys Res Commun* 2000, 275, 678-681.
S. Dimon-Gadal, P. Gerbaud, P. Therond, J. Guibourdenche, W. B. Anderson, D. Evain-Brion and F. Raynaud, *J Invest Dermatol* 2000, 114, 984-989.
A. Dhar, K. M. Desai, L. Wu, *British journal of pharmacology* 2010, 159, 166-175.
M. J. Eberhardt, M. R. Filipovic, A. Leffler, J. de la Roche, K. Kistner, M. J. Fischer, T. Fleming, K. Zimmermann, I. Ivanovic-Burmazovic, P. P. Nawroth, A. Bierhaus, P. W. Reeh, S. K. Sauer, *The Journal of biological chemistry* 2012, 287, 28291-28306.
L. Engelen, C. D. Stehouwer, C. G. Schalkwijk, *Diabetes, obesity & metabolism* 2013, 15, 677-689.
R. J. Ferrante, S. E. Browne, L. A. Shinobu, A. C. Bowling, M. J. Baik, U. MacGarvey, N. W. Kowall, R. H. Brown, Jr. and M. F. Beal, *J Neurochem* 1997, 69, 2064-2074.
T. Fleming, J. Cuny, G. Nawroth, Z. Djuric, P. M. Humpert, M. Zeier, A. Bierhaus, P. P. Nawroth, *Diabetologia* 2012, 55, 1151-1155.
E. Floor and M. G. Wetzel, *J Neurochem* 1998, 70, 268-275.
J. M. Forbes, M. E. Cooper, *Physiol Rev* 2013, 93, 137-188.
S. Genuth, W. Sun, P. Cleary, X. Gao, D. R. Sell, J. Lachin, D. E. R. Group, V. M. Monnier. *Diabetes* 2015, 64, 266-278.
F. Giacco, X. Du, V. D. D'Agati, R. Milne, G. Sui, M. Geoffrion and M. Brownlee, *Diabetes* 2014, 63, 291-299.
K. Hensley, N. Hall, R. Subramaniam, P. Cole, M. Harris, M. Aksenov, M. Aksenova, S. P. Gabbita, J. F. Wu, J. M. Carney and et al., *J Neurochem* 1995, 65, 2146-2156.
J. Himmelfarb and E. McMonagle, *Kidney Int* 2001, 60, 358-363.

J. Himmelfarb, E. McMonagle and E. McMenamin, *Kidney Int* 2000, 58, 2571-2578.

I. Jonassen, S. Havelund, T. Hoeg-Jensen, D. B. Steensgaard, P. O. Wahlund, U. Ribel, *Pharmaceutical research* 2012, 29, 2104-2114.

O. R. Kinsky, T. L. Hargraves, T. Anumol, N. E. Jacobsen, J. Dai, S. A. Snyder, T. J. Monks, S. S. Lau, *Chemical research in toxicology* 2016, 29, 227-234.

R. E. Kontermann, *Current opinion in biotechnology* 2011, 22, 868-876.

A. Lapolla, R. Flamini, A. Lupo, N. C. Arico, C. Rugiu, R. Reitano, M. Tubaro, E. Ragazzi, R. Seraglia and P. Traldi, *Ann N Y Acad Sci* 2005, 1043, 217-224.

P. Li, P. P. Roller, *Current topics in medicinal chemistry* 2002, 2, 325-341.

P. S. Lim, Y. M. Cheng and Y. H. Wei, *Free Radic Res* 2002, 36, 295-301.

J. Lobner, J. Degen, T. Henle, *Journal of agricultural and food chemistry* 2015, 63, 2249-2256.

T. W. Lo, T. Selwood, P. J. Thornalley, *Biochemical pharmacology* 1994, 48, 1865-1870.

T. W. Lo, M. E. Westwood, A. C. McLellan, T. Selwood, P. J. Thornalley, *The Journal of biological chemistry* 1994, 269, 32299-32305.

L. Lyras, R. H. Perry, E. K. Perry, P. G. Ince, A. Jenner, P. Jenner and B. Halliwell, *J Neurochem* 1998, 71, 302-312.

D. E. Maessen, C. D. Stehouwer and C. G. Schalkwijk, *Clin Sci (Lond)* 2015, 128, 839-861.

D. Mantle, G. Falkous and D. Walker, *Clin Chim Acta* 1999, 284, 45-58.

L. T. McGrath, P. Mallon, L. Dowey, B. Silke, E. McClean, M. McDonnell, A. Devine, S. Copeland and S. Elborn, *Thorax* 1999, 54, 518-523.

T. Miyata, C. van Ypersele de Strihou, K. Kurokawa and J. W. Baynes, *Kidney Int* 1999, 55, 389-399.

T. Miyata, Y. Ueda, A. Saito and K. Kurokawa, *Nephrol Dial Transplant* 2000, 15 Suppl 1, 25-28.

S. Muller-Krebs, L. P. Kihm, B. Zeier, M. L. Gross, R. Deppisch, A. Wieslander, T. Henle, I. Penndorf, J. Oh, J. Reiser, P. P. Nawroth, M. Zeier and V. Schwenger, *Eur J Clin Invest* 2008, 38, 296-305.

G. Munch, B. Kuhla, H. J. Luth, T. Arendt and S. R. Robinson, *Biochem Soc Trans* 2003, 31, 1397-1399.

R. Nagai, K. Mera, K. Nakajou, Y. Fujiwara, Y. Iwao, H. Imai, T. Murata, M. Otagiri, *Biochimica et biophysica acta* 2007, 1772, 1192-1198.

R. H. Nagaraj, P. Sarkar, A. Mally, K. M. Biemel, M. O. Lederer, P. S. Padayatti, *Archives of biochemistry and biophysics* 2002, 402, 110-119.

K. Nakayama, M. Nakayama, M. Iwabuchi, H. Terawaki, T. Sato, M. Kohno and S. Ito, *Am J Nephrol* 2008, 28, 871-878.

U. Pantke, T. Volk, M. Schmutzler, W. J. Kox, N. Sitte and T. Grune, *Free Radic Biol Med* 1999, 27, 1080-1086.

N. Rabbani, K. Sebekova, K. Sebekova, Jr., A. Heidland and P. J. Thornalley, *Kidney Int* 2007, 72, 1113-1121.

N. Rabbani, P. J. Thornalley, *Nature protocols* 2014, 9, 1969-1979.

N. Rabbani and P. J. Thornalley, *Biochemical and Biophysical Research Communications* 2015, 458, 221-226.

N. Rabbani, M. V. Chittari, C. W. Bodmer, D. Zehnder, A. Ceriello and P. J. Thornalley, *Diabetes* 2010 59, 1038-1045.

N. Rabbani, L. Godfrey, M. Xue, F. Shaheen, M. Geoffrion, R. Milne and P. J. Thornalley, *Diabetes* 2011 60, 1973-1980.

S. P. Range, C. Dunster, A. J. Knox and F. J. Kelly, *Eur Respir J* 1999, 13, 560-564.

J. Renke, S. Popadiuk, M. Korzon, B. Bugajczyk and M. Wozniak, *Free Radic Biol Med* 2000, 29, 101-104.

Schalkwijk, C. G., M. A. Vermeer, C. D. Stehouwer, J. to Koppele, H. M. Princen and V. W. van Hinsbergh, *Biochim Biophys Acta*, 1998 1394, 187-198.

F. A. Shamsi, K. Lin, C. Sady and R. H. Nagaraj, *Invest Ophthalmol Vis Sci* 1998, 39, 2355-2364.

K. Shinpo, S. Kikuchi, H. Sasaki, A. Ogata, F. Moriwaka and K. Tashiro, *Brain Res* 2000, 861, 151-159.

P. J. Thornalley, S. Battah, N. Ahmed, N. Karachalias, S. Agalou, R. Babaei-Jadidi, A. Dawnay, *The Biochemical journal* 2003, 375, 581-592.

T. Uchiki, K. A. Weikel, W. Jiao, F. Shang, A. Caceres, D. Pawlak, J. T. Handa, M. Brownlee, R. Nagaraj, A. Taylor, *Aging cell* 2012, 11, 1-13.

G. Vistoli, M. Orioli, A. Pedretti, L. Regazzoni, R. Canevotti, G. Negrisoli, M. Carini, G. Aldini, *ChemMedChem* 2009, 4, 967-975.

T. Wang, R. Kartika, D. A. Spiegel, *Journal of the American Chemical Society* 2012, 134, 8958-8967.

C. C. Winterbourn, I. H. Buss, T. P. Chan, L. D. Plank, M. A. Clark and J. A. Windsor, *Crit Care Med* 2000, 28, 143-149.

Wischnjow, D. Sarko, M. Janzer, C. Kaufman, B. Beijer, S. Brings, U. Haberkorn, G. Larbig, A. Kubelbeck, W. Mier, *Bioconjug Chem* 2016.

G. Yang, G. I. Cancino, S. K. Zahr, A. Guskjolen, A. Voronova, D. Gallagher, P. W. Frankland, D. R. Kaplan and F. D. Miller, *Cell Reports* 2016, 17, 1022-1036.

P. L. Zusterzeel, H. Rutten, H. M. Roelofs, W. H. Peters and E. A. Steegers, *Placenta* 2001, 22, 213-219.

The invention claimed is:

1. A cyclic peptide comprising the amino acid sequence of $$Xaa_m\text{-}(Arg)_n\text{-}Glu_o$$

wherein Xaa is selected from Lys, ornithine (2,5-diaminopentanoic acid); 2,4-diaminobutanoic acid; and 2,3-diaminopropanoic acid; wherein
m is at least 1,
n is selected from 2 to 8,
o is 1;
and a hydrophobic modification attached to the side chain of Xaa, wherein the hydrophobic modification is an acylation with a C12 to C22 fatty acid, an acylation with a C12 to C22 dicarboxylic acid, or an acylation with a fatty acid containing phenyl group,
and wherein said cyclic peptide is cyclized via
(a) head-to-side chain cyclization,
(b) head-to-tail cyclization,
(c) backbone cyclization,
(d) amide condensation of two amino acid side chains,
(e) thioether formation, and/or
(f) side chain-to-tail cyclization.

2. The cyclic peptide according to claim 1, wherein the hydrophobic modification is attached to the side chain of Xaa via a linker.

3. The cyclic peptide according to claim 1, wherein the hydrophobic modification is
an acylation with a C12 to C22 fatty acid, which is attached via the side chain of $Xaa_m$, wherein Xaa=Lys and m=1,
an acylation with a C12 to C22 dicarboxylic acid, which is attached via a linker to the side chain of $Xaa_m$, wherein Xaa=Lys and m=1 and wherein the linker is an amino acid, or
an acylation with a phenyl containing fatty acid.

4. The cyclic peptide according to claim 1, of the formula

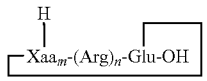

wherein
Xaa is Lys; ornithine (2,5-diaminopentanoic acid); 2,4-diaminobutanoic acid; or 2,3-diaminopropanoic acid, wherein
m is at least 1,
n is 4, and
H is the hydrophobic modification, wherein the hydrophobic modification is attached to the side chain of Xaa, optionally via a linker.

5. The cyclic peptide according to claim 1, being selected from

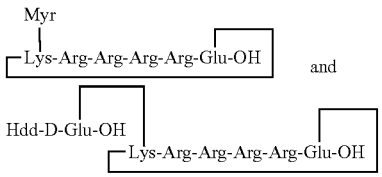

wherein Myr is myristoyl and Hdd is hexadecanedioic acid.

6. The cyclic peptide according to claim 1, which inhibits the binding of methylglyoxal (MG) and/or reactive carbonyl species (RCS) to an arginine- or lysine-containing protein.

7. A pharmaceutical composition comprising
at least one cyclic peptide according to claim 1, and
a pharmaceutically acceptable carrier and/or excipient.

8. The cyclic peptide, according to claim 1, wherein the acylation is with myristoyl, hexadecanedioc acid, or 4-(p-iodophenyl)butyric acid.

9. The cyclic peptide, according to claim 4, wherein said compound is

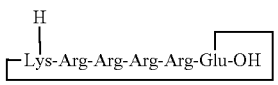

wherein
H is attached to the side chain of Lys and is selected from myristoyl or linker-hexadecanedioic acid, wherein the linker is D-Glu.

* * * * *

UNITED STATES PATENT AND TRADEMARK OFFICE
CERTIFICATE OF CORRECTION

PATENT NO. : 11,202,833 B2
APPLICATION NO. : 16/345094
DATED : December 21, 2021
INVENTOR(S) : Sebastian Brings et al.

It is certified that error appears in the above-identified patent and that said Letters Patent is hereby corrected as shown below:

In the Specification

Column 7,
Line 33, "Hdd-d-Glu-OH" should read --Hdd-D-Glu-OH--
Line 40, "(-Hdd)R$_4$E" should read --(e-Hdd) R$_4$E--

Column 8,
Line 53, "the kidney." should read --the kidney,--
Line 57, "the kidney." should read --the kidney,--

Column 10,
Line 20, "MG levels" should read --MG levels.--

Column 15,
Line 50, "150 mmol" should read --150 mmol/L--

Column 18,
Line 22, "and 4=120-140" should read --t$_4$=120-140--

Column 25,
Line 40, "samples was" should read --samples were--

Column 28,
Lines 21-22, "J. to Koppele," should read --J. te Koppele,--

Signed and Sealed this
Seventh Day of March, 2023

Katherine Kelly Vidal
*Director of the United States Patent and Trademark Office*

SEQUENCE LISTING

<160> NUMBER OF SEQ ID NOS: 20

<210> SEQ ID NO 1
<211> LENGTH: 6
<212> TYPE: PRT
<213> ORGANISM: Artificial Sequence
<220> FEATURE:
<223> OTHER INFORMATION: Cyclic peptide cycKR4E, wherein the side chain
      of K carries a hydrophobic moiety, such as Myr or Hdd-D-Glu

<400> SEQUENCE: 1

Lys Arg Arg Arg Arg Glu
1               5

```
<210> SEQ ID NO 2
<211> LENGTH: 5
<212> TYPE: PRT
<213> ORGANISM: Artificial Sequence
<220> FEATURE:
<223> OTHER INFORMATION: pentapeptide

<400> SEQUENCE: 2

Ala Arg Arg Ala Ala
1               5

<210> SEQ ID NO 3
<211> LENGTH: 5
<212> TYPE: PRT
<213> ORGANISM: Artificial Sequence
<220> FEATURE:
<223> OTHER INFORMATION: pentapeptide

<400> SEQUENCE: 3

Ala Lys Arg Ala Ala
1               5

<210> SEQ ID NO 4
<211> LENGTH: 5
<212> TYPE: PRT
<213> ORGANISM: Artificial Sequence
<220> FEATURE:
<223> OTHER INFORMATION: pentapeptide

<400> SEQUENCE: 4

Ala Cys Arg Ala Ala
1               5

<210> SEQ ID NO 5
<211> LENGTH: 5
<212> TYPE: PRT
<213> ORGANISM: Artificial Sequence
<220> FEATURE:
<223> OTHER INFORMATION: pentapeptide

<400> SEQUENCE: 5

Ala Val Arg Ala Ala
1               5

<210> SEQ ID NO 6
<211> LENGTH: 5
<212> TYPE: PRT
<213> ORGANISM: Artificial Sequence
<220> FEATURE:
<223> OTHER INFORMATION: pentapeptide

<400> SEQUENCE: 6

Ala Gln Arg Ala Ala
1               5

<210> SEQ ID NO 7
<211> LENGTH: 5
<212> TYPE: PRT
<213> ORGANISM: Artificial Sequence
<220> FEATURE:
<223> OTHER INFORMATION: pentapeptide

<400> SEQUENCE: 7

Ala Tyr Arg Ala Ala
1               5
```

```
<210> SEQ ID NO 8
<211> LENGTH: 5
<212> TYPE: PRT
<213> ORGANISM: Artificial Sequence
<220> FEATURE:
<223> OTHER INFORMATION: pentapeptide

<400> SEQUENCE: 8

Ala Trp Arg Ala Ala
1               5

<210> SEQ ID NO 9
<211> LENGTH: 5
<212> TYPE: PRT
<213> ORGANISM: Artificial Sequence
<220> FEATURE:
<223> OTHER INFORMATION: pentapeptide

<400> SEQUENCE: 9

Ala Ala Arg Ala Ala
1               5

<210> SEQ ID NO 10
<211> LENGTH: 5
<212> TYPE: PRT
<213> ORGANISM: Artificial Sequence
<220> FEATURE:
<223> OTHER INFORMATION: pentapeptide

<400> SEQUENCE: 10

Ala Asn Arg Ala Ala
1               5

<210> SEQ ID NO 11
<211> LENGTH: 5
<212> TYPE: PRT
<213> ORGANISM: Artificial Sequence
<220> FEATURE:
<223> OTHER INFORMATION: pentapeptide

<400> SEQUENCE: 11

Ala Phe Arg Ala Ala
1               5

<210> SEQ ID NO 12
<211> LENGTH: 5
<212> TYPE: PRT
<213> ORGANISM: Artificial Sequence
<220> FEATURE:
<223> OTHER INFORMATION: pentapeptide

<400> SEQUENCE: 12

Ala Met Arg Ala Ala
1               5

<210> SEQ ID NO 13
<211> LENGTH: 5
<212> TYPE: PRT
<213> ORGANISM: Artificial Sequence
<220> FEATURE:
<223> OTHER INFORMATION: pentapeptide

<400> SEQUENCE: 13

Ala Leu Arg Ala Ala
1               5

<210> SEQ ID NO 14
```

```
<211> LENGTH: 5
<212> TYPE: PRT
<213> ORGANISM: Artificial Sequence
<220> FEATURE:
<223> OTHER INFORMATION: pentapeptide

<400> SEQUENCE: 14

Ala His Arg Ala Ala
1               5

<210> SEQ ID NO 15
<211> LENGTH: 5
<212> TYPE: PRT
<213> ORGANISM: Artificial Sequence
<220> FEATURE:
<223> OTHER INFORMATION: pentapeptide

<400> SEQUENCE: 15

Ala Ser Arg Ala Ala
1               5

<210> SEQ ID NO 16
<211> LENGTH: 5
<212> TYPE: PRT
<213> ORGANISM: Artificial Sequence
<220> FEATURE:
<223> OTHER INFORMATION: pentapeptide

<400> SEQUENCE: 16

Ala Asp Arg Ala Ala
1               5

<210> SEQ ID NO 17
<211> LENGTH: 5
<212> TYPE: PRT
<213> ORGANISM: Artificial Sequence
<220> FEATURE:
<223> OTHER INFORMATION: pentapeptide

<400> SEQUENCE: 17

Ala Glu Arg Ala Ala
1               5

<210> SEQ ID NO 18
<211> LENGTH: 40
<212> TYPE: PRT
<213> ORGANISM: Artificial Sequence
<220> FEATURE:
<223> OTHER INFORMATION: MG scavenger peptide GERP10

<400> SEQUENCE: 18

Gly Glu Arg Pro Gly Glu Arg Pro Gly Glu Arg Pro Gly Glu Arg Pro
1               5                   10                  15

Gly Glu Arg Pro Gly Glu Arg Pro Gly Glu Arg Pro Gly Glu Arg Pro
            20                  25                  30

Gly Glu Arg Pro Gly Glu Arg Pro
        35                  40

<210> SEQ ID NO 19
<211> LENGTH: 41
<212> TYPE: PRT
<213> ORGANISM: Artificial Sequence
<220> FEATURE:
<223> OTHER INFORMATION: K-GERP10

<400> SEQUENCE: 19
```

```
Lys Gly Glu Arg Pro Gly Glu Arg Pro Gly Glu Arg Pro Gly Glu Arg
1               5                  10                 15

Pro Gly Glu Arg Pro Gly Glu Arg Pro Gly Glu Arg Pro Gly Glu Arg
            20                  25                  30

Pro Gly Glu Arg Pro Gly Glu Arg Pro
        35                  40

<210> SEQ ID NO 20
<211> LENGTH: 7
<212> TYPE: PRT
<213> ORGANISM: Artificial Sequence
<220> FEATURE:
<223> OTHER INFORMATION: Cyclic peptide cycKR4E (as in SEQ ID NO. 1)
      with an additional N-terminal K

<400> SEQUENCE: 20

Lys Lys Arg Arg Arg Arg Glu
1               5
```